United States Patent
Nguyen et al.

(10) Patent No.: US 11,696,751 B2
(45) Date of Patent: Jul. 11, 2023

(54) TISSUE REPAIR DEVICES

(71) Applicant: Smith & Nephew, Inc., Memphis, TN (US)

(72) Inventors: Linh Tuong Nguyen, Randolph, MA (US); Paul S. Vincuilla, Brockton, MA (US); Richard M. Lunn, Kingston, MA (US); Mark E. Housman, North Attleboro, MA (US); Matthew E. Koski, Westford, MA (US); Roland F. Gatturna, Bourne, MA (US); David A. Paulk, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 268 days.

(21) Appl. No.: 16/924,425

(22) Filed: Jul. 9, 2020

(65) Prior Publication Data

US 2020/0337690 A1 Oct. 29, 2020

Related U.S. Application Data

(60) Continuation of application No. 15/793,448, filed on Oct. 25, 2017, now Pat. No. 10,743,855, which is a division of application No. 12/943,086, filed on Nov. 10, 2010, now Pat. No. 9,936,939.

(60) Provisional application No. 61/334,221, filed on May 13, 2010, provisional application No. 61/312,481, filed on Mar. 10, 2010, provisional application No. 61/290,695, filed on Dec. 29, 2009, provisional application No. 61/259,737, filed on Nov. 10, 2009, (Continued)

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0412* (2013.01); *A61B 2017/0414* (2013.01); *A61B 2017/0435* (2013.01); *A61B 2017/0441* (2013.01); *A61B 2017/0445* (2013.01); *A61B 2017/0448* (2013.01); *A61B 2017/0453* (2013.01); *A61B 2017/0464* (2013.01)

(58) Field of Classification Search
CPC .... A61B 2017/0409; A61B 2017/0412; A61B 2017/0414; A61B 2017/0441; A61B 2017/0445; A61B 2017/0448; A61B 2017/0464
See application file for complete search history.

(56) References Cited

U.S. PATENT DOCUMENTS

2003/0105489 A1\* 6/2003 Eichhorn ............. A61F 2/0811
606/232
2004/0138706 A1\* 7/2004 Abrams ............ A61B 17/0401
606/232

(Continued)

*Primary Examiner* — Alexander J Orkin
(74) *Attorney, Agent, or Firm* — Norman F. Hainer, Jr.; Kate Ryland Tetzlaff

(57) ABSTRACT

The present disclosure relates to an anchor assembly. The anchor assembly includes an anchor defining a cavity and an opening to the cavity; and a headless insertion member configured for arrangement within the anchor cavity, the insertion member including a body having a threaded proximal portion, a non-threaded distal portion, and a cannulation extending a partial length of the insertion member. Other anchor assemblies, anchors, and delivery devices are also disclosed.

20 Claims, 42 Drawing Sheets

Related U.S. Application Data provisional application No. 61/259,739, filed on Nov. 10, 2009.

(56) References Cited

U.S. PATENT DOCUMENTS

| | | | |
|---|---|---|---|
| 2005/0055052 A1* | 3/2005 | Lombardo | A61B 17/0401 606/232 |
| 2006/0079904 A1* | 4/2006 | Thal | A61F 2/0811 606/232 |
| 2008/0033486 A1* | 2/2008 | Whittaker | A61B 17/0401 606/232 |
| 2008/0086138 A1* | 4/2008 | Stone | A61B 17/0401 606/265 |
| 2008/0275469 A1* | 11/2008 | Fanton | A61B 17/0469 606/232 |
| 2009/0234387 A1* | 9/2009 | Miller | A61B 17/0401 606/232 |
| 2010/0094355 A1* | 4/2010 | Trenhaile | A61B 17/0401 606/232 |
| 2010/0292733 A1* | 11/2010 | Hendricksen | A61B 17/0401 606/232 |
| 2010/0318125 A1* | 12/2010 | Gerber | A61B 17/0401 606/232 |

\* cited by examiner

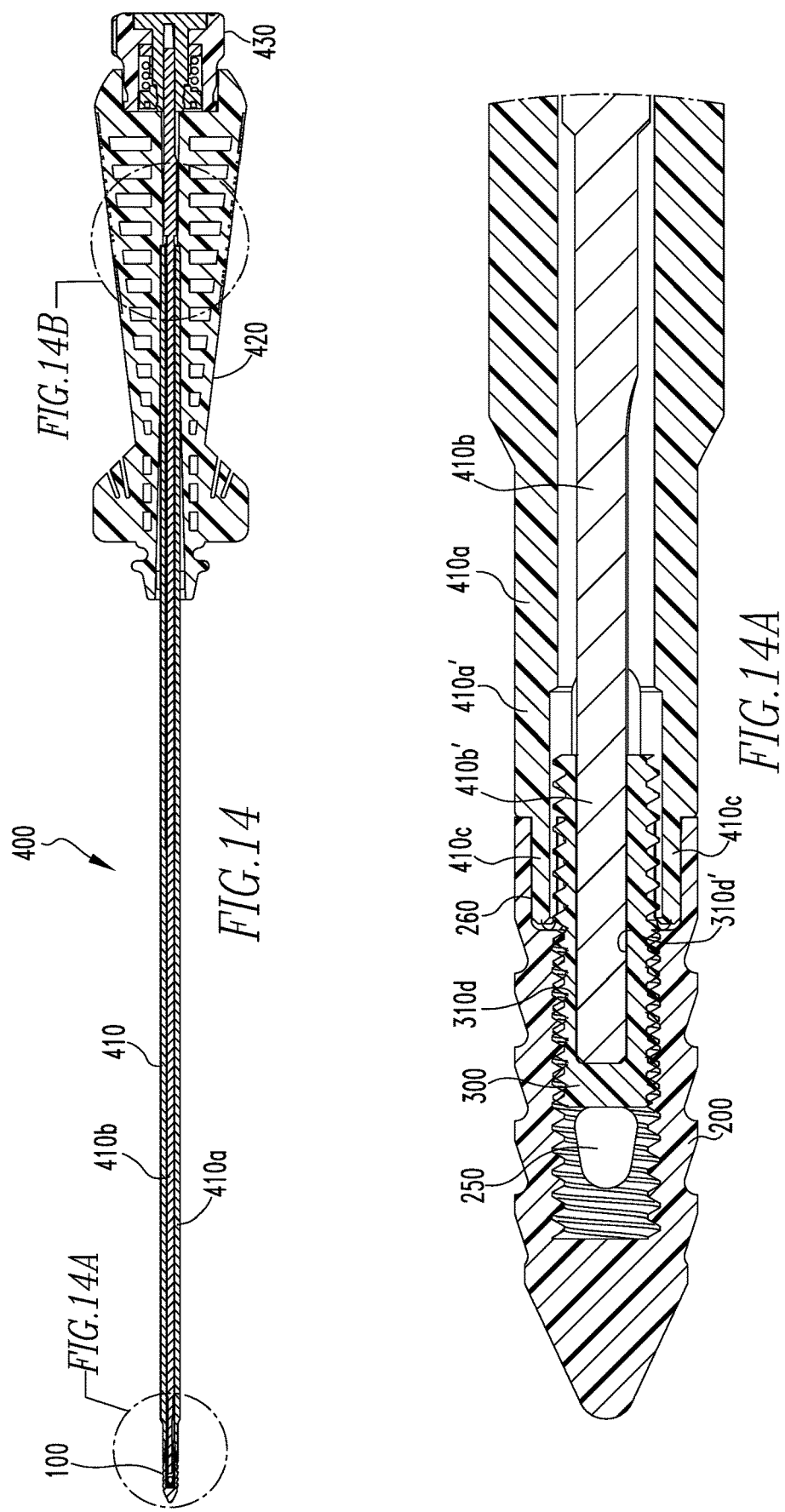

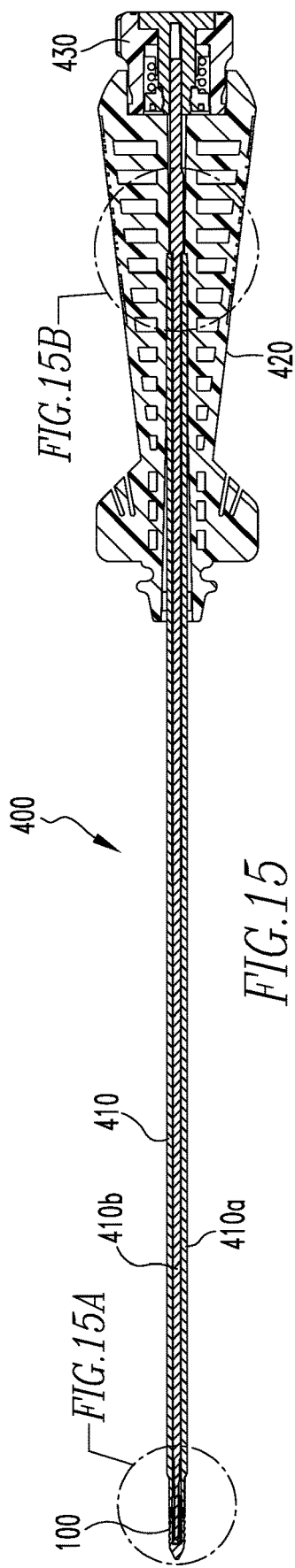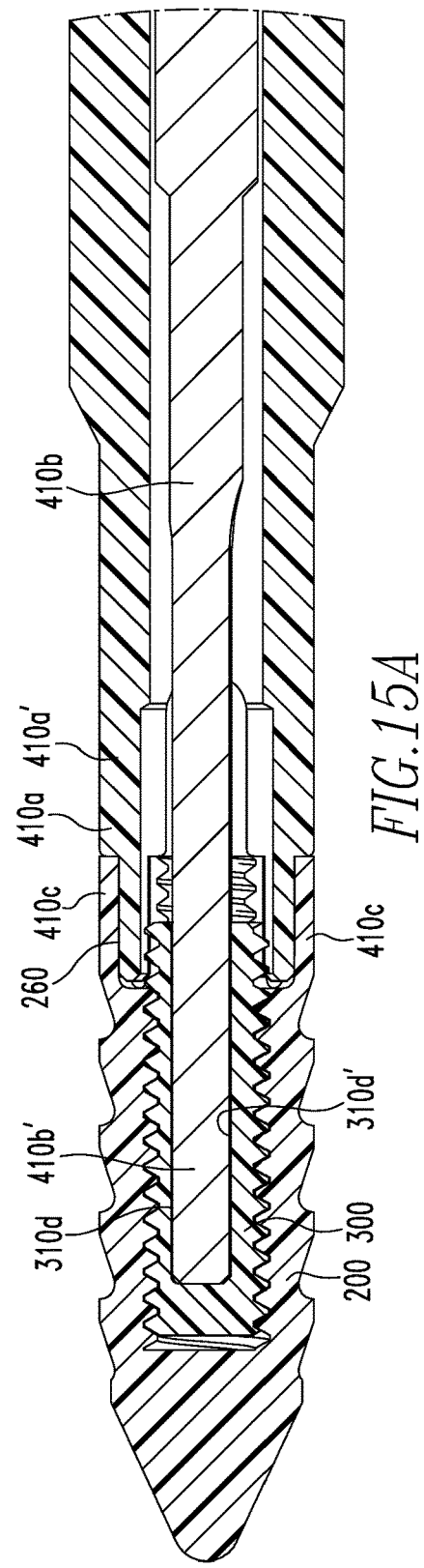

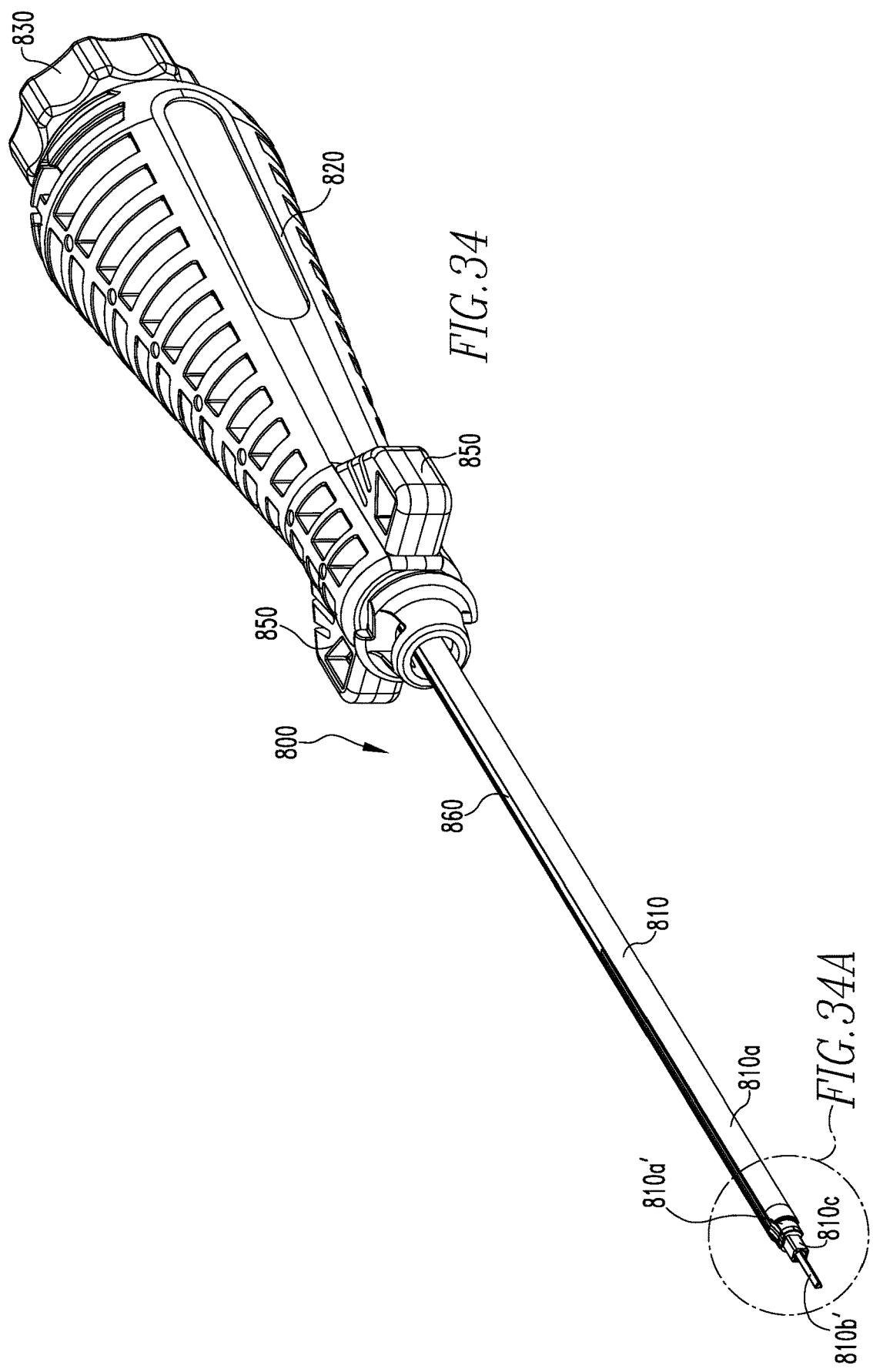

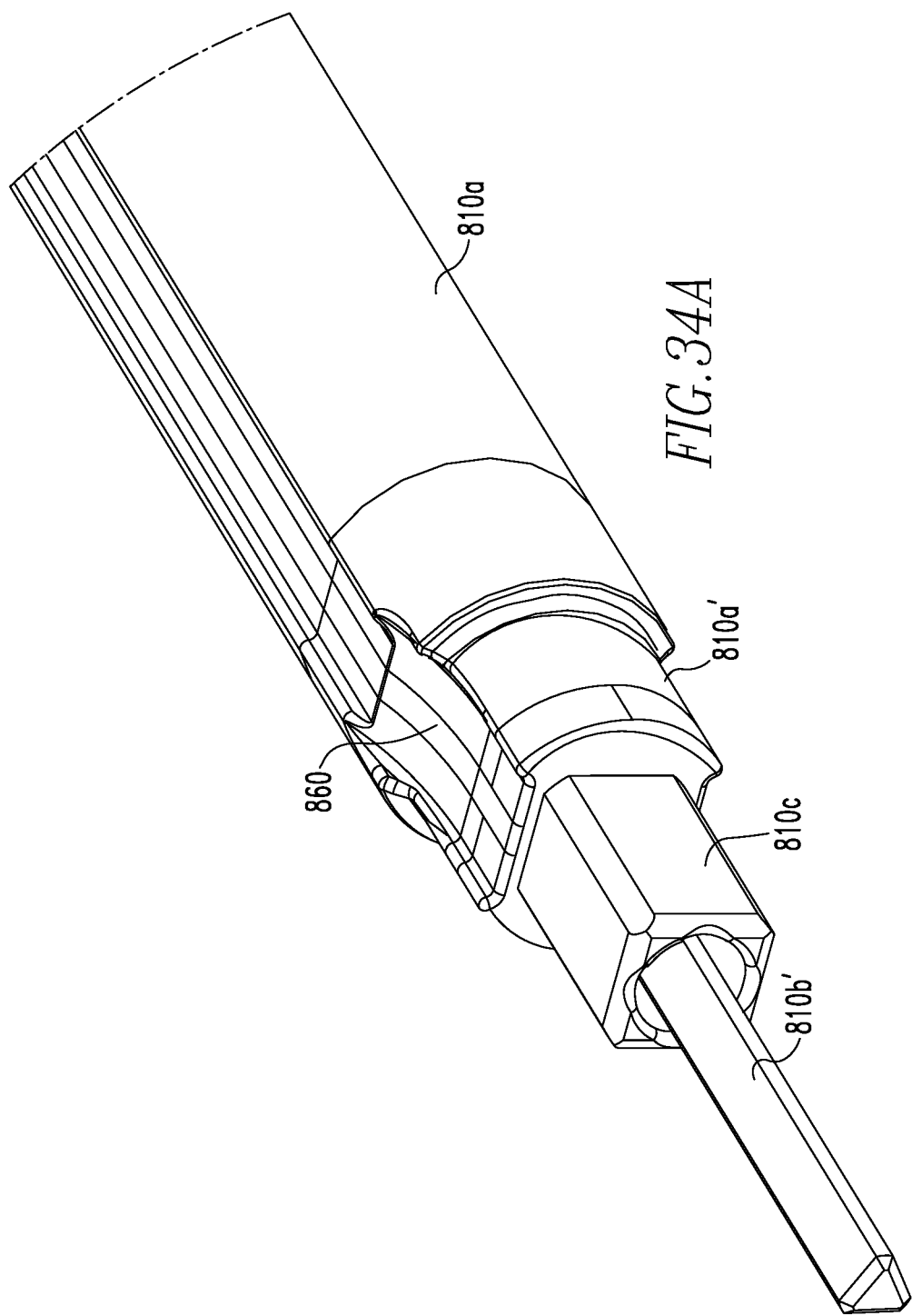

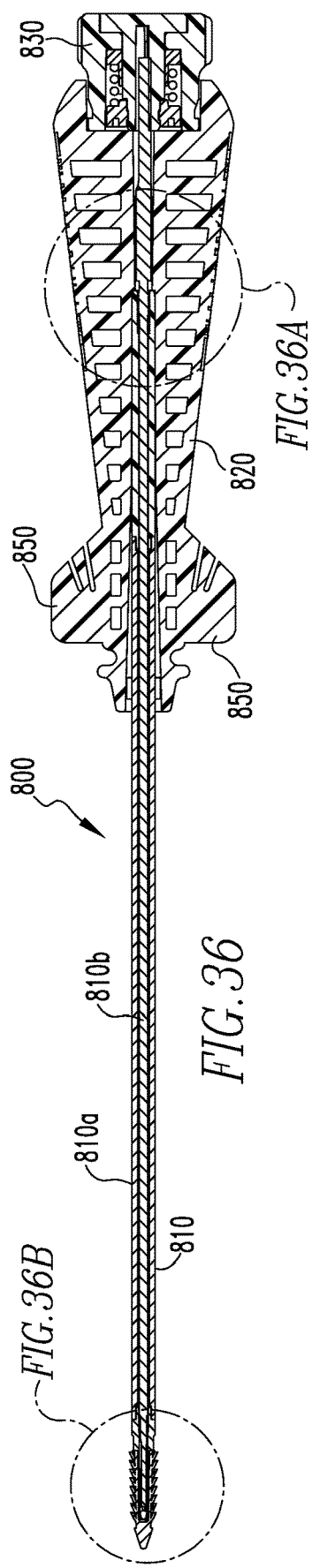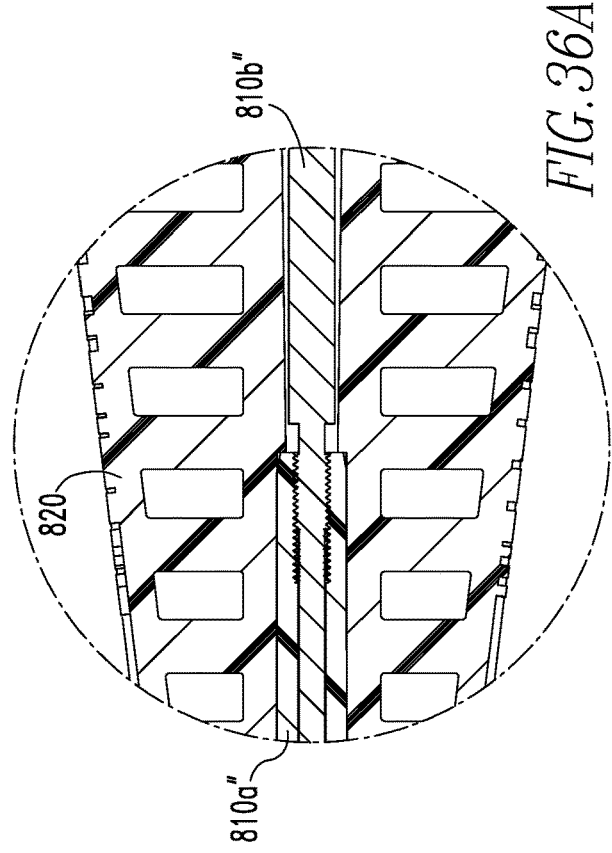

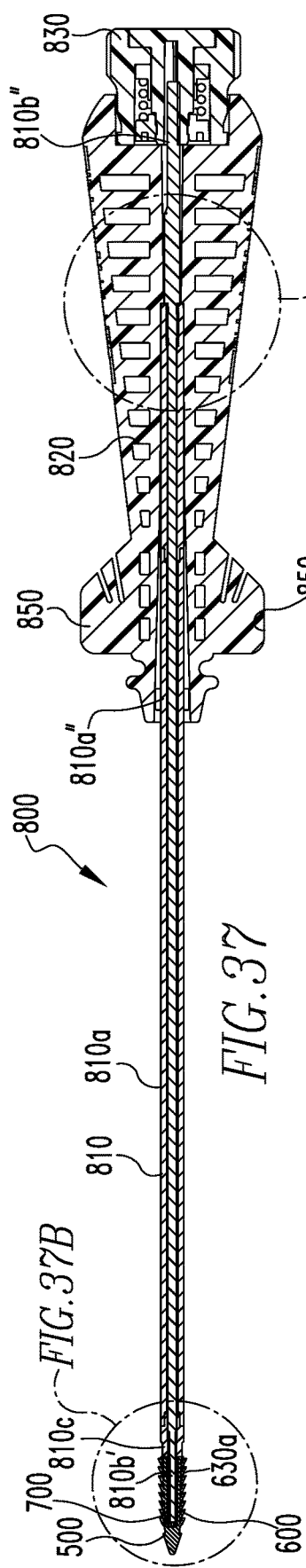
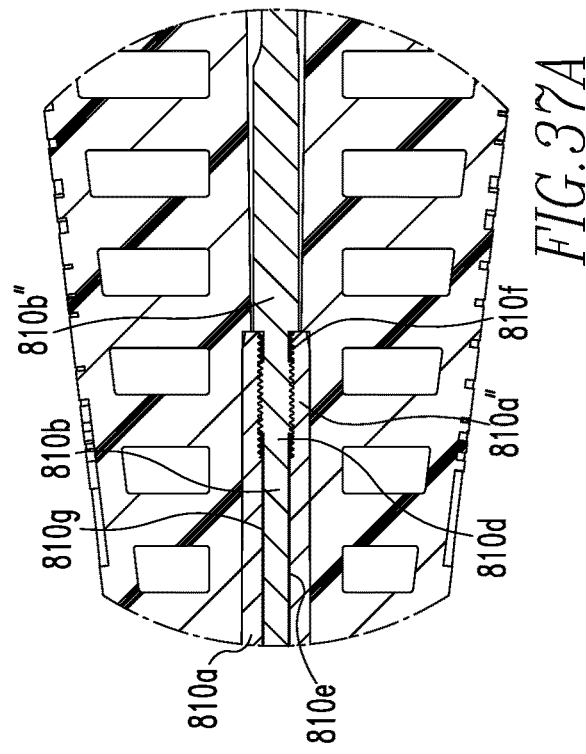

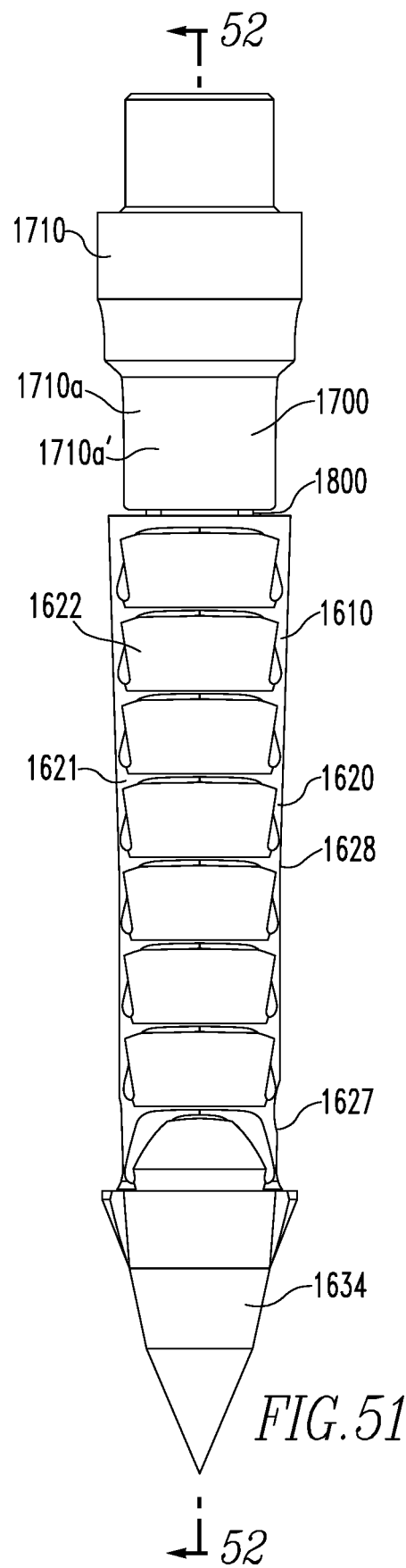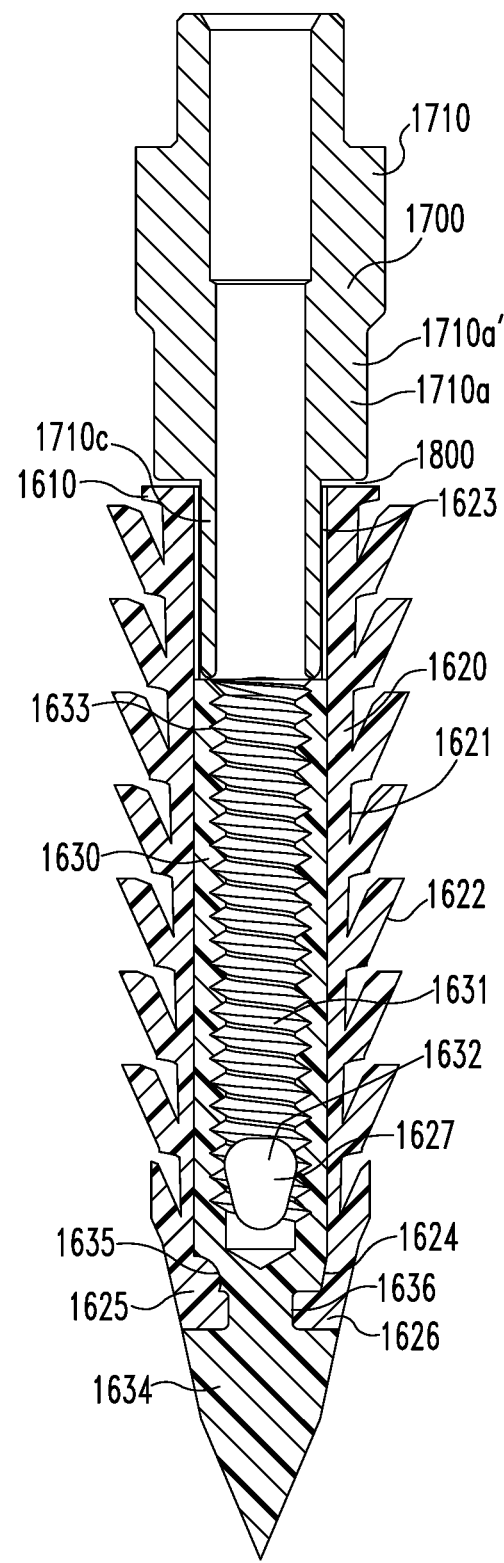
FIG.51
FIG.52

TISSUE REPAIR DEVICES

CROSS-REFERENCE TO RELATED APPLICATIONS

This application is a continuation of U.S. application Ser. No. 15/793,448 filed Oct. 25, 2017, which claims priority to U.S. application Ser. No. 12/943,086 filed Nov. 10, 2010, now U.S. Pat. No. 9,936,939, which claims priority to U.S. Patent Application No. 61/259,737, filed Nov. 10, 2009. U.S. Patent Application No. 61/259,739, filed Nov. 10, 2009, U.S. Patent Application No. 61/290,695, filed Dec. 29, 2009, U.S. Patent Application No. 61/312,481 filed Mar. 10, 2010, and US Patent Application No. 61/334,221, filed May 13, 2010, the disclosures of which are incorporated herein by reference in their entireties.

BACKGROUND

Field of Technology

The present disclosure relates to tissue repair devices, and more specifically, to anchors, anchor assemblies, and delivery devices for use in securing tissue to bone.

Related Art

Arthroscopic procedures often require soft tissue to be reattached to bone. To achieve this, anchors are placed in the bone and sutures attached to the anchor are passed through the tissue to securely retain the tissue in place. A procedure and components for use in such procedure, that securely attaches tissue to bone, is needed. Such procedure must be able to be done in a quick and efficient manner with a minimum of recovery time for the patient.

SUMMARY

In an aspect, the present disclosure relates to an anchor assembly. The anchor assembly includes an anchor defining a cavity and an opening to the cavity; and a headless insertion member configured for arrangement within the anchor cavity, the insertion member including a body having a threaded proximal portion, a non-threaded distal portion, and a cannulation extending a partial length of the insertion member. In an embodiment, the cannulation is triangular shaped. In another embodiment, the anchor cavity includes a threaded proximal portion and a non-threaded distal portion. In yet another embodiment, the distal portion of the insertion member includes two segments and a tapered portion located between the segments.

In another aspect, the present disclosure relates to an anchor assembly. The anchor assembly includes an anchor defining a cavity and an opening to the cavity and a headless insertion member configured for arrangement within the anchor cavity, the insertion member including a fully threaded body and a cannulation extending a partial length of the insertion member.

In yet another aspect, the present disclosure relates to a surgical device. The surgical device includes a shaft including an outer member and an inner member slidably received within the outer member, the outer member including an inner surface having threads and the inner member including an outer surface having threads; a handle coupled to the shaft; and a knob coupled to the inner member, wherein the threads of the inner member and the threads of the outer member are engaged to allow for coupling of the inner member and the outer member and movement of the outer member relative to the inner member upon rotation of the knob. In an embodiment, the inner member is triangular-shaped. In another embodiment, the inner member includes a depth stop. In yet another embodiment, the outer member includes a tip extending from an end of the outer member. In a further embodiment, the tip is square-shaped.

In a further aspect, the present disclosure relates to an anchor assembly. The anchor assembly including an anchor defining a cavity and an opening to the cavity, the cavity including a non-threaded proximal portion and a threaded distal portion; and a headless insertion member configured for arrangement within the anchor cavity, the insertion member including a body and a cannulation extending a partial length of the insertion member, the body including a threaded proximal portion and a non-threaded distal portion. In an embodiment, the proximal portion is square-shaped.

In yet a further aspect, the present disclosure relates to an anchor. The anchor includes a body defining a cavity and an opening to the cavity, the body including an outer surface and channels extending from the outer surface to the cavity. In an embodiment, the body includes barbs, the channels located between the barbs. In another embodiment, the outer surface includes slots, the slots intersecting the barbs.

In an aspect, the present disclosure relates to an anchor assembly. The anchor assembly including an anchor defining a cavity and an opening to the cavity, the anchor including a body having an outer surface and barbs extending from the body and alternating in direction along the length of the body; and a headless insertion member configured for arrangement within the anchor cavity, the insertion member including a body and a cannulation extending a partial length of the insertion member.

In another aspect, the present disclosure relates to an anchor assembly. The anchor assembly includes an anchor including an outer body and an inner body coupled to the outer body, the outer body including a first feature and a second feature, the inner body including a first feature and a second feature, the first feature of the inner body and the first feature of the outer body engaged to allow for non-rotation of the inner body relative to the outer body and the second feature of the inner body and the second feature of the outer body engaged to allow for non-movement of the inner body relative to the outer body in an axial direction; and a headless insertion member configured for arrangement within the inner body, the insertion member including a body and a cannulation extending a partial length of the insertion member.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 14 shows a cross-sectional view of the delivery device and anchor assembly of FIG. 13 prior to use of the device and assembly during surgery.

FIG. 14A shows an exploded view of the distal end of the delivery device and the anchor assembly of FIG. 14.

FIG. 15 shows a cross-sectional view of the delivery device and anchor assembly of FIG. 13 after use of the device and assembly during surgery.

FIG. 15A shows an exploded view of the distal end of the delivery device and the anchor assembly of FIG. 15.

FIG. 34 shows an isometric view of the delivery device for use with the anchor assembly of FIG. 28.

FIG. 34A shows an exploded view of the distal end of the delivery device of FIG. 34.

FIG. 36 shows a cross-sectional view of the delivery device and anchor assembly of FIG. 35 prior to use of the device and assembly during surgery.

FIG. 36A shows an exploded view of the proximal ends of the outer and inner members of the delivery device of FIG. 36.

FIG. 37 shows a cross-sectional view of the delivery device and anchor assembly of FIG. 35 after to use of the device and assembly during surgery.

FIG. 37A shows an exploded view of the proximal ends of the outer and inner members of the delivery device of FIG. 37.

FIG. 51 shows a side view of a seventh embodiment of the anchor assembly of the present disclosure.

FIG. 52 shows a cross-sectional view of the anchor assembly of FIG. 51.

DETAILED DESCRIPTION OF THE EMBODIMENTS

The following description of the preferred embodiment(s) is merely exemplary in nature and is in no way intended to limit the disclosure, its application, or uses.

Figure 1:
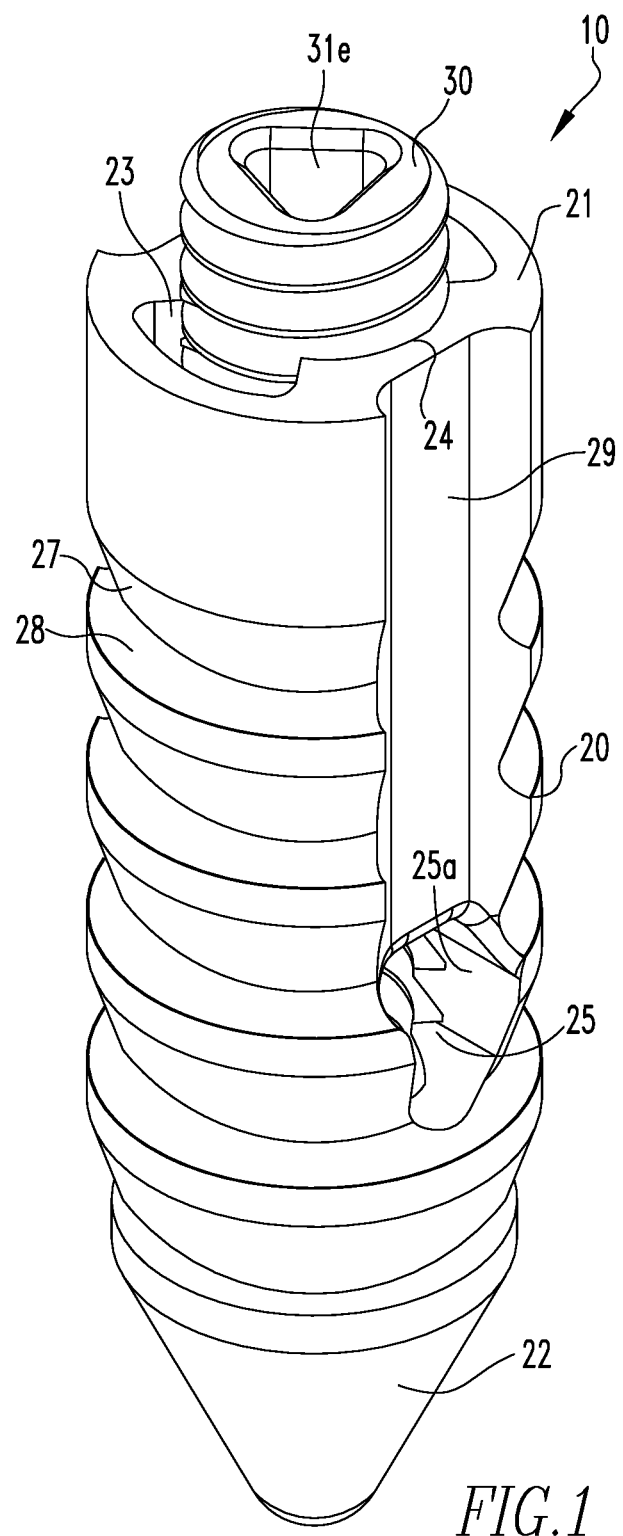
FIG. 1 shows a side elevational view of a first embodiment of the anchor assembly of the present disclosure.
Figure 2A:
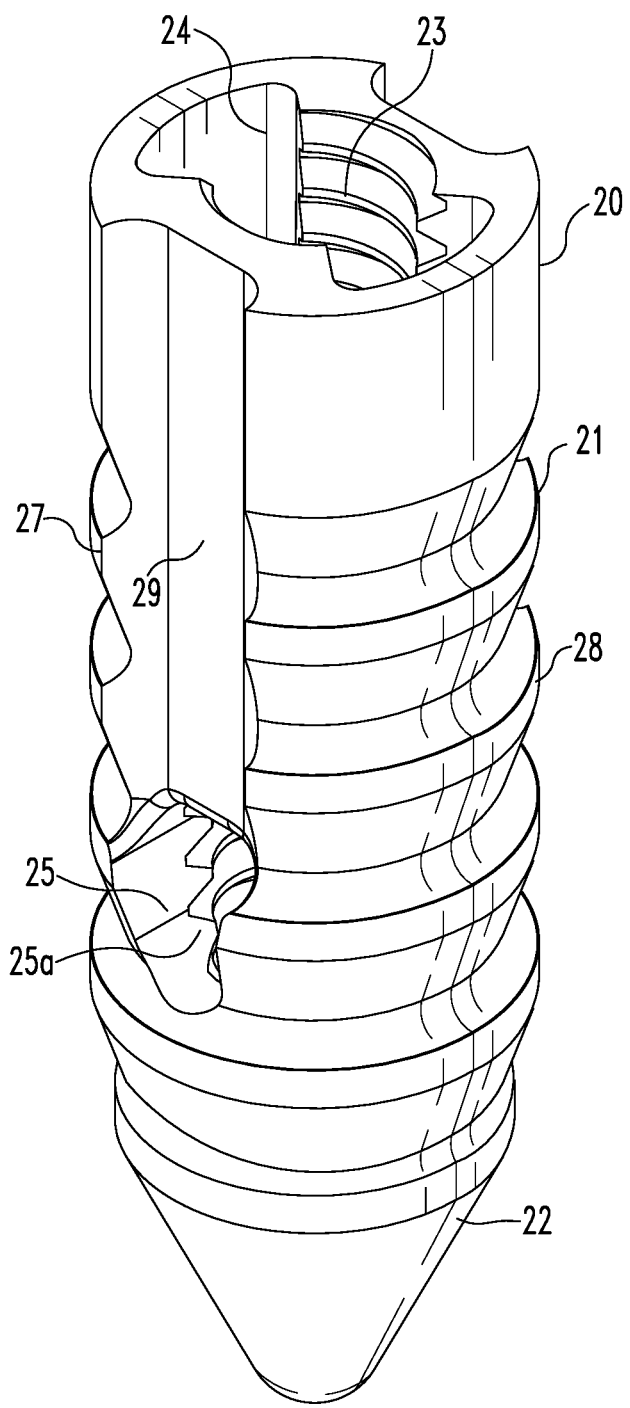
FIG. 2A shows a side elevational view of the anchor of the anchor assembly of FIG. 1.
Figure 2B:
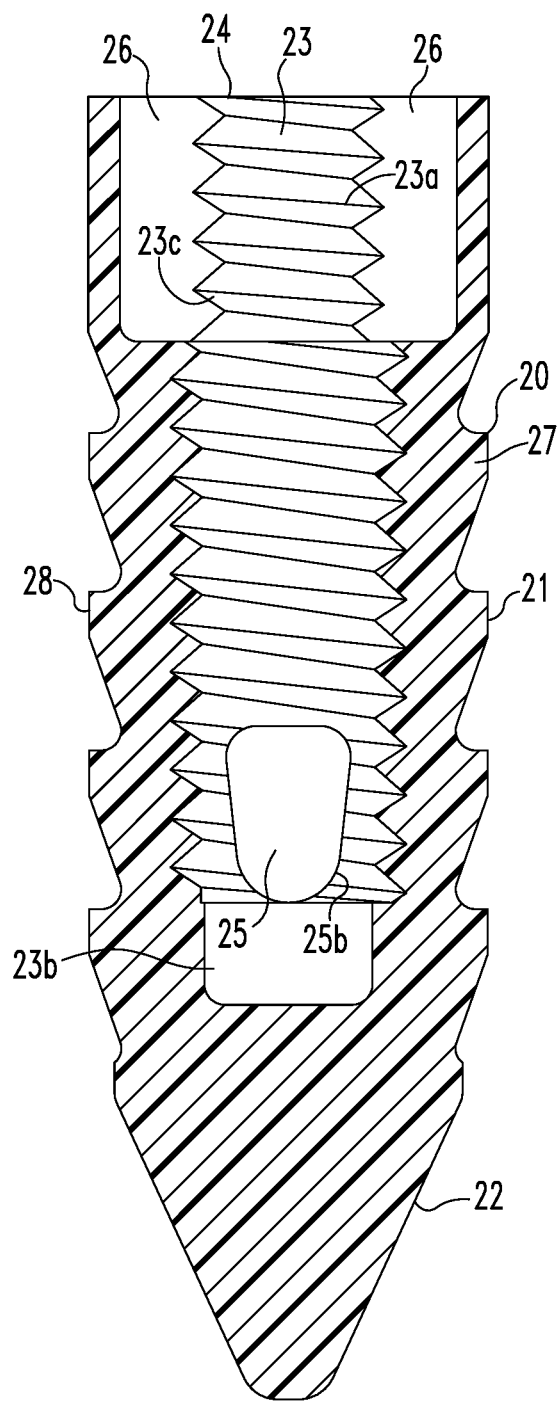
FIG. 2B shows a cross-sectional view of the anchor of FIG. 2A.

FIGS. 1, 2A-2B, and 3A-3B show a first embodiment of the anchor assembly 10 of the present disclosure and its components. The assembly 10 includes the anchor 20 and the insertion member 30. The anchor 20 includes a proximal portion 21, a distal portion 22, and an inner cavity 23. An opening 24 to the cavity 23 is located at the proximal portion 21 of the anchor 20. The anchor 20 also includes a transverse hole 25 extending through the anchor 20. The through hole 25 is for housing of a flexible member, such as suture. Openings 25a,b are located at each end of the through hole 25. The outer surface 27 of the proximal portion 21 also includes barbs 28 for substantially reducing the possibility of removal of the anchor 20 when inserted into bone. The outer surface 27 also includes at least two slots 29 extending from the openings 25a,b of the through hole 25. The slots 29 intersect the barbs 28 and are configured for housing of the suture after positioning of the anchor 20 in bone. As shown in FIG. 2B, the cavity 23 extends into and beyond the through hole 25 and includes a threaded proximal portion 23a and a non-threaded distal portion 23b. Also shown in FIG. 2B are a pair of depressions 26, each of which is located adjacent to the cavity 23. The depressions 26 are for housing of a delivery device, as will be further explained later.

Figure 3A:
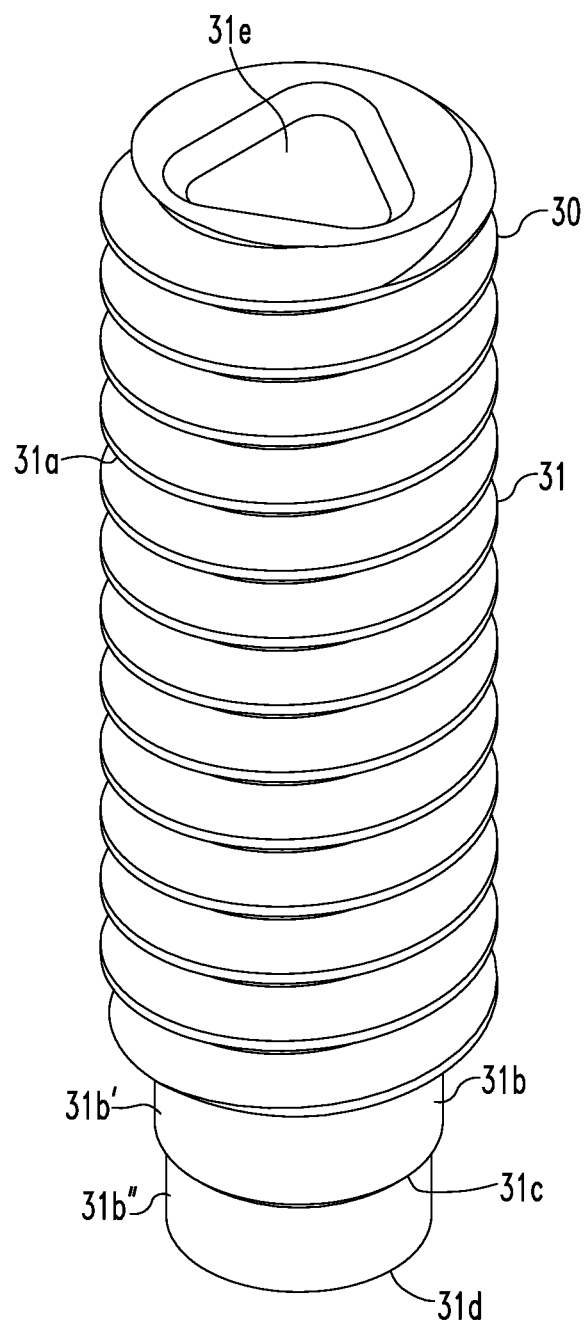
FIG. 3A shows a side elevational view of the insertion member of the anchor assembly of FIG. 1.
Figure 3B:
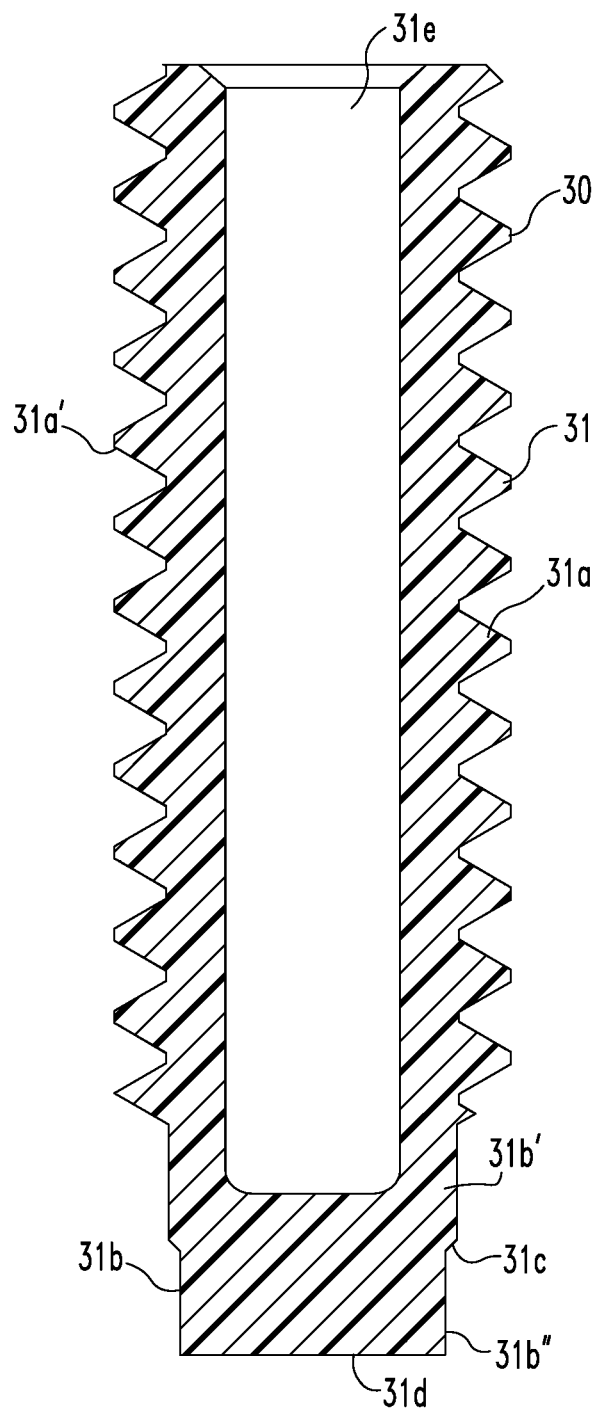
FIG. 3B shows a cross-sectional view of the insertion member of FIG. 3A.
Figure 4:
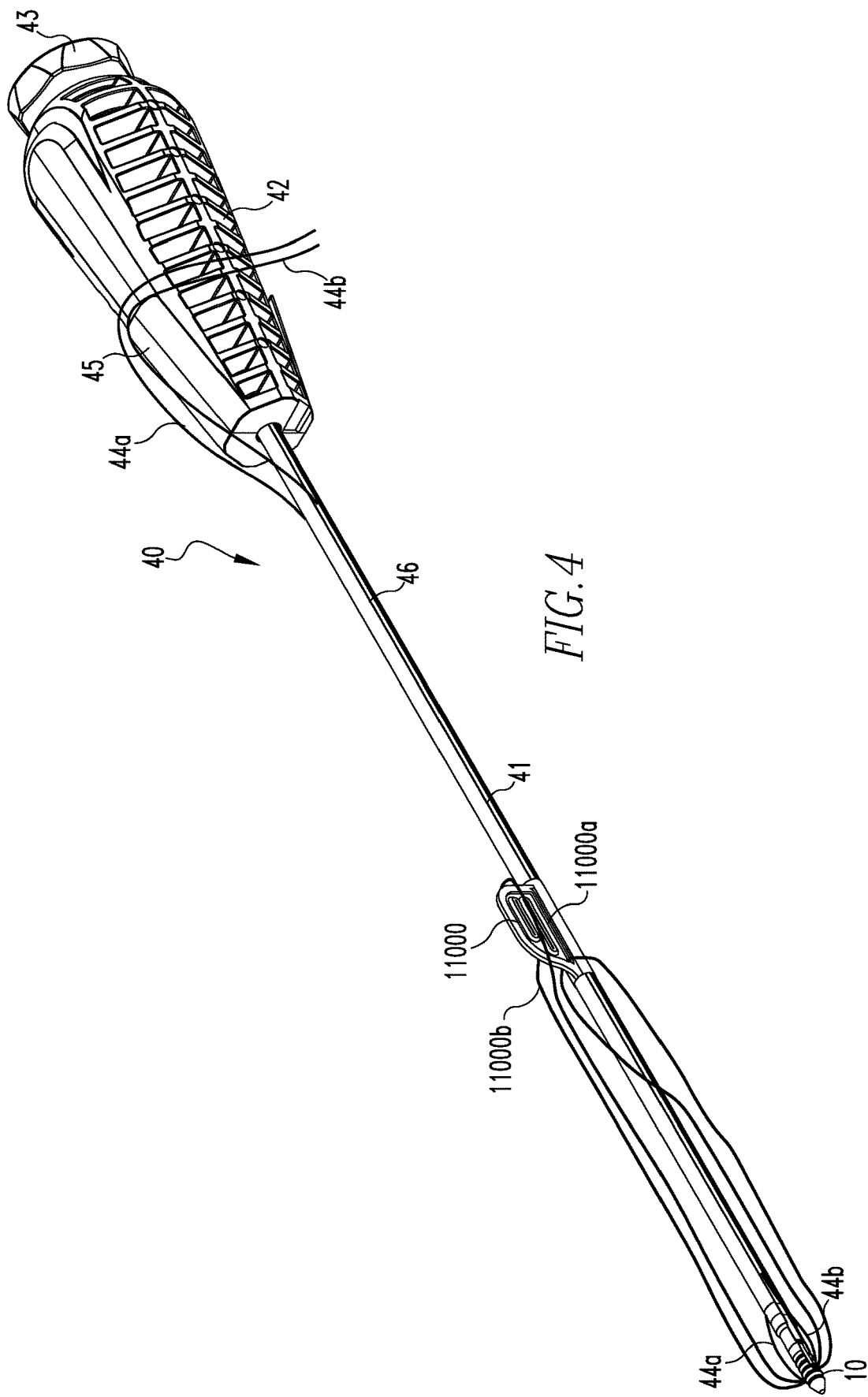
FIG. 4 shows an isometric view of the delivery device of the present disclosure.

The insertion member 30 includes a headless body 31 having a threaded proximal portion 31a and a non-threaded distal portion 31b. The distal portion 31b includes two segments 31b', 31b" and a tapered portion 31c located between the segments 31b', 31b". Segment 31b" has a flat end portion 31d. As shown in FIGS. 3A and 3B, the member 30 includes a triangular-shaped cannulation 31e that extends a partial length of the member 30. The threads 31a' are configured for engagement with the threads 23c of the cavity 23 when the insertion member 30 is arranged within the cavity 23, as will be further explained below.

FIGS. 4-7 show the delivery device 40 of the present disclosure. The device 40 includes a shaft 41, a handle 42 coupled to the shaft 41, and a knob 43 coupled to the handle 42. The shaft 41 includes an outer member 41a and an inner member 41b slidably disposed within and coupled to the outer member 41a. The inner member 41b includes a distal end 41b' configured for disposal within the cannulation 31e of the insertion member 30 and a proximal end 41b" coupled to the knob 43. The end 41b' is of a diameter such that it engages the wall 31e' of the cannulation 31e, thereby allowing movement of the member 30 when the knob 43 is rotated, as will be further described below. The outer member 41a includes prongs 41c located at a distal end 41a' of the outer member 41a and a proximal end 41a" coupled to the handle 42.

Prior to use, suture 44 is disposed within the through hole 25 and ends 44a,44b of the suture 44 are fixed to suture holders 45 located on handle 42. The suture 44 helps to keep anchor 20 coupled to the shaft 41. The delivery device 40 and its components, especially the handle 42 and knob 43, is similar to the delivery device shown and described in US Patent Application Publication 20100016869, the disclosure of which is incorporated herein by reference in its entirety. The ends 44a,44b of the suture 44 are also housed within channels 46 that extend along the shaft 41. A suture threader 11000 is also releasably coupled to the shaft 41. Threader 11000 includes a clip 11000a and a loop of suture 11000b coupled to the clip 11000a. Suture loop 11000b is disposed within the through hole 25 and placed around the clip 11000a.

Figure 5:
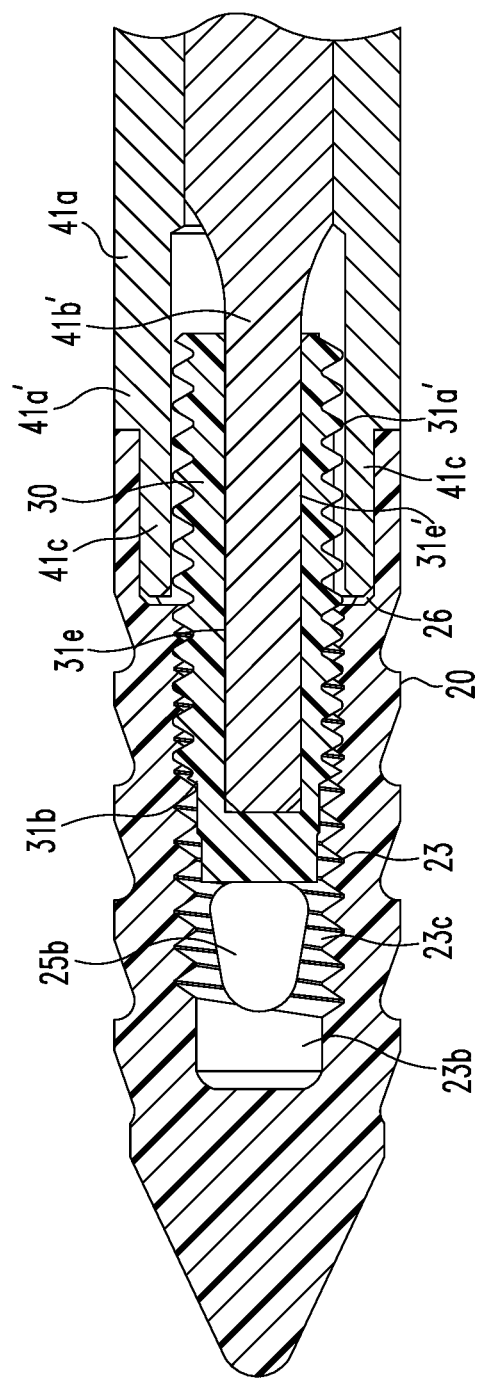
FIG. 5 shows a cross-sectional view of the distal ends of the outer and inner members of the delivery device of FIG. 4 and the anchor assembly of FIG. 1 prior to fixation of suture.
Figure 6:
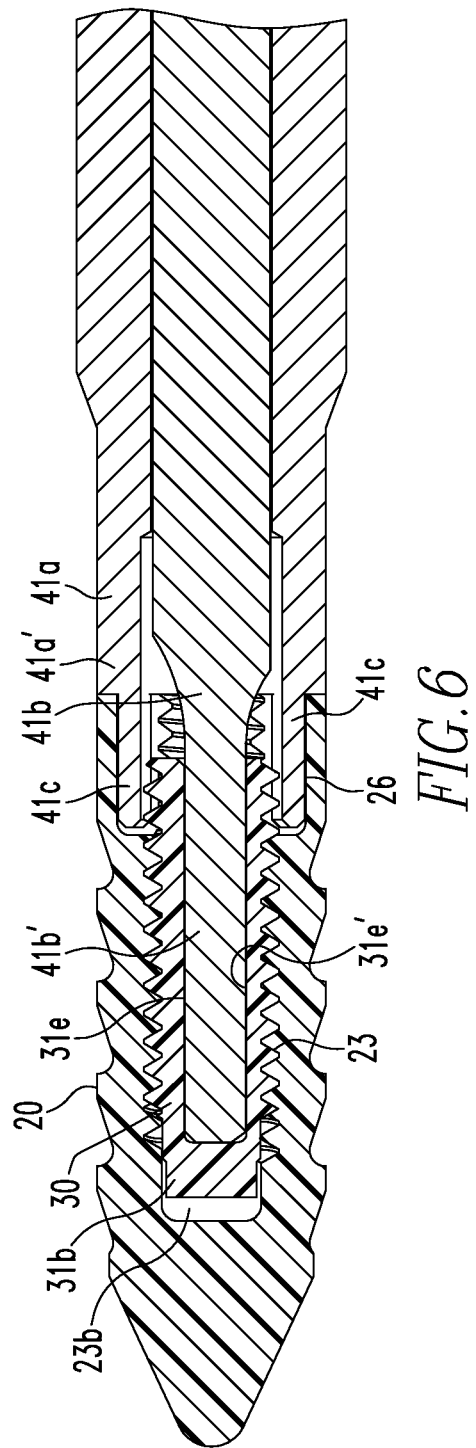
FIG. 6 shows a cross-sectional view of the distal ends of the outer and inner members of the delivery device of FIG. 4 and the anchor assembly of FIG. 1 after fixation of suture.

As shown in FIG. 5, the prongs 41c are disposed within the depressions 26. Once the anchor assembly 10 is disposed within bone, the prongs 41c help to hold the anchor 20 stationary while the insertion member 30 is moved relative to the anchor 20 via rotation of the knob 43. As will be further described below, FIG. 5 shows the location of the insertion member 30 prior to fixation of suture within the cavity 23, while FIG. 6 shows the location of the insertion member 30 after fixation of suture within the cavity 23. The non-threaded distal portion 31b is configured to be housed within the non-threaded distal portion 23b of the anchor 20.

Figure 7:
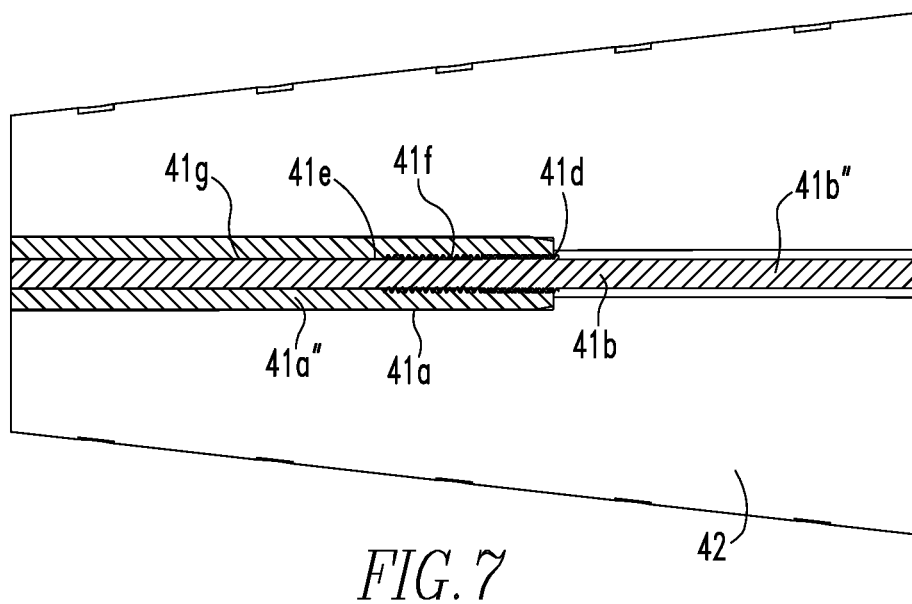
FIG. 7 shows a cross-sectional view of the proximal ends of the outer and inner members of the delivery device of FIG. 4.

Additionally, as shown in FIG. 7, the proximal end 41b" of the inner member 41b includes threads 41d on an outer surface 41e of the inner member 41b and the proximal end 41a" of the outer member 41a includes threads 41f on an inner surface 41g of the outer member 41a. Threads 41f engage threads 41d to allow for coupling of the outer and inner members 41a, 41b and axial movement of the inner member 41b relative to the outer member 41a, via rotation of the knob 43. Axial movement of the inner member 41b relative to the outer member 41a allows for axial movement of the insertion member 30 to the two locations shown in FIGS. 5 and 6.

Figure 10:
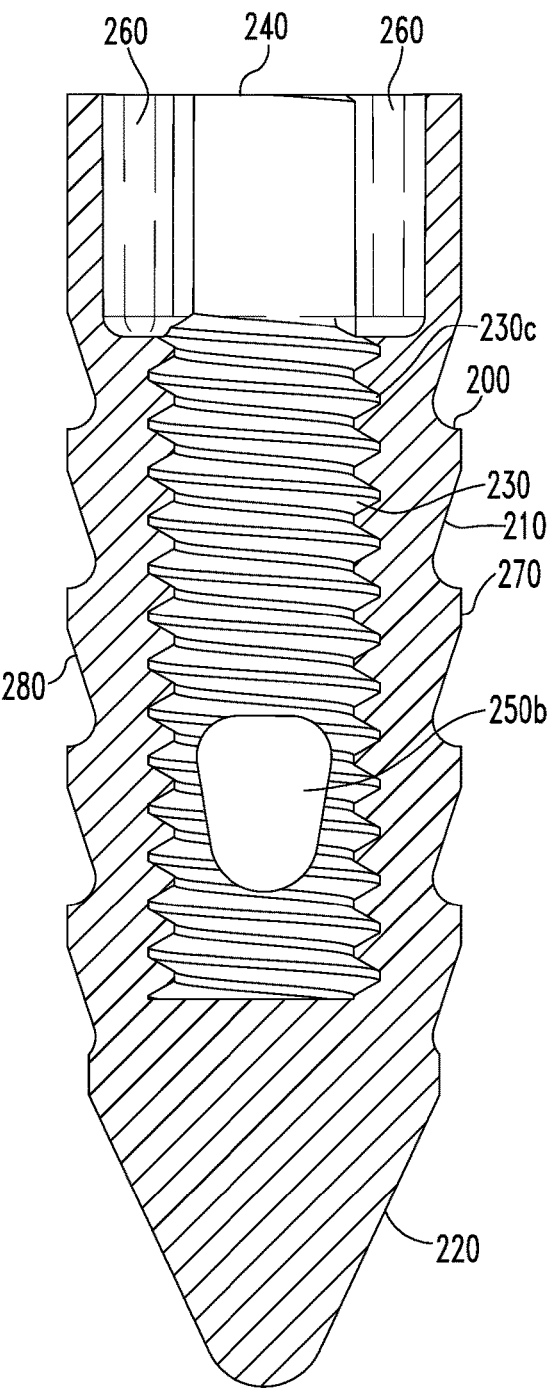
FIG. 10 shows a cross-sectional view of the anchor of FIG. 9.

FIGS. 8-12 show a second embodiment of the anchor assembly 100 of the present disclosure and its components. The assembly 100 includes the anchor 200 and the insertion member 300. The anchor 200 includes a proximal portion 210, a distal portion 220, and an inner cavity 230. An opening 240 to the cavity 230 is located at the proximal portion 210 of the anchor 200. The anchor 200 also includes a transverse hole 250 extending through the anchor 200. The through hole 250 is for housing of a flexible member, such as suture. Openings 250a,b are located at each end of the through hole 250. The outer surface 270 of the proximal portion 210 also includes barbs 280 for substantially reducing the possibility of removal of the anchor 200 when inserted into bone. The outer surface 270 also includes at least two slots 290 extending from the openings 250a,b of the through hole 250. The slots 290 intersect the barbs 280 and are configured for housing of the suture after positioning of the anchor 200 in bone. As shown in FIG. 10, the cavity 230 extends into and beyond the through hole 250. Also shown in FIG. 10 are a pair of depressions 260, each of which is located adjacent to the cavity 230. The depressions 260 are for housing of a delivery device, as will be further explained later.

Figure 8:
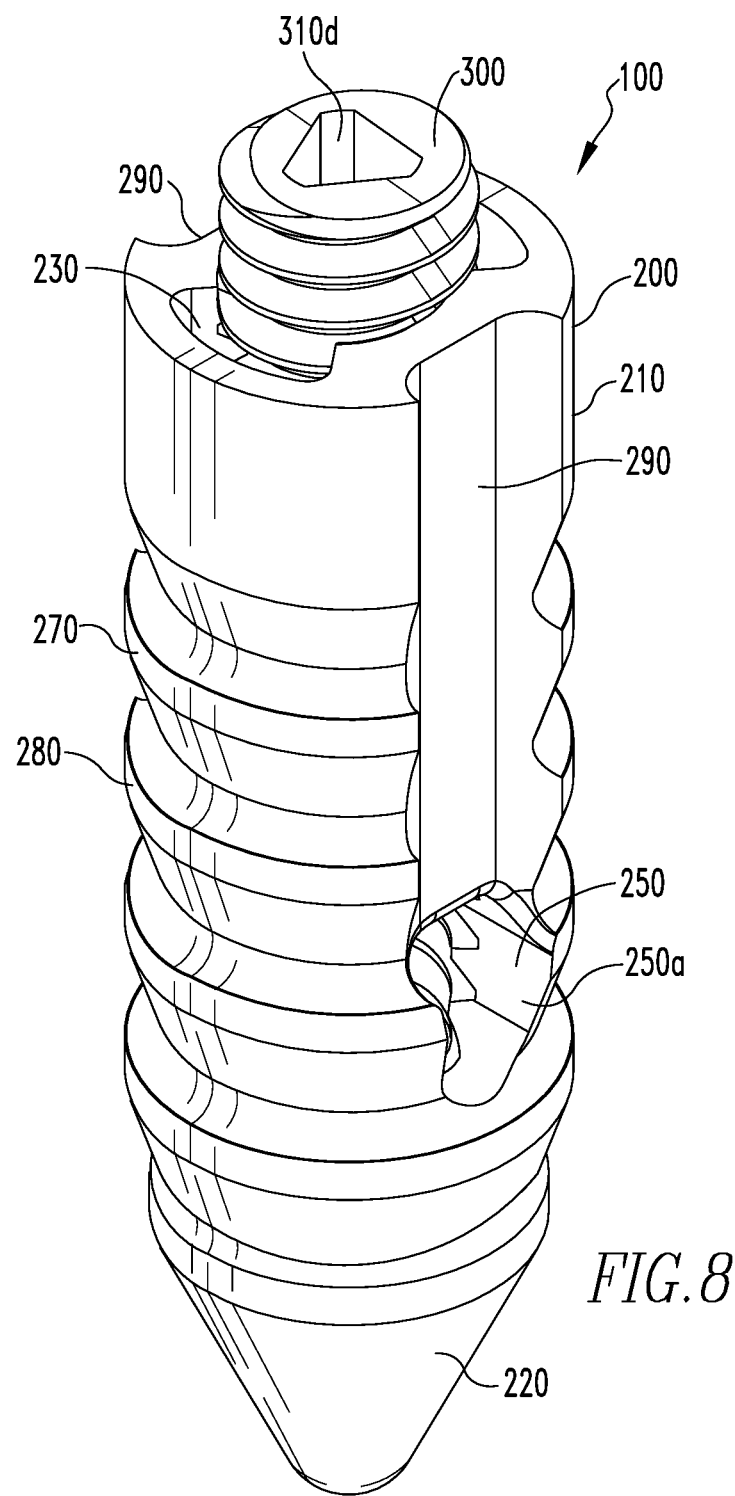
FIG. 8 shows a side elevational view of a second embodiment of the anchor assembly of the present disclosure.
Figure 9:
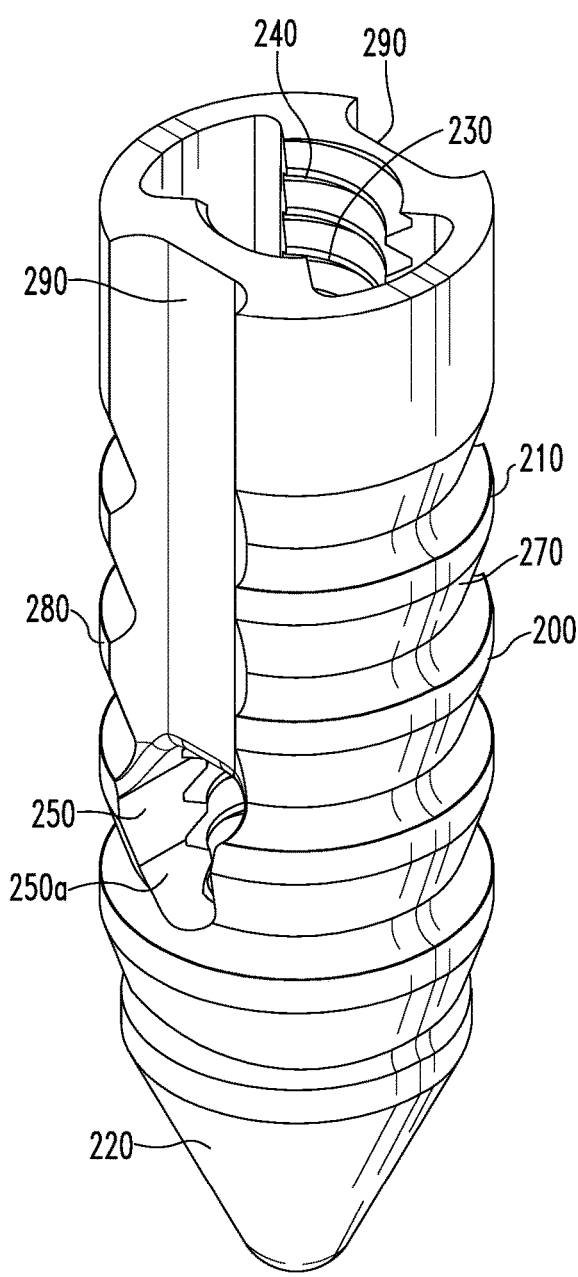
FIG. 9 shows a side elevational view of the anchor of the anchor assembly of FIG. 8.
Figure 11:
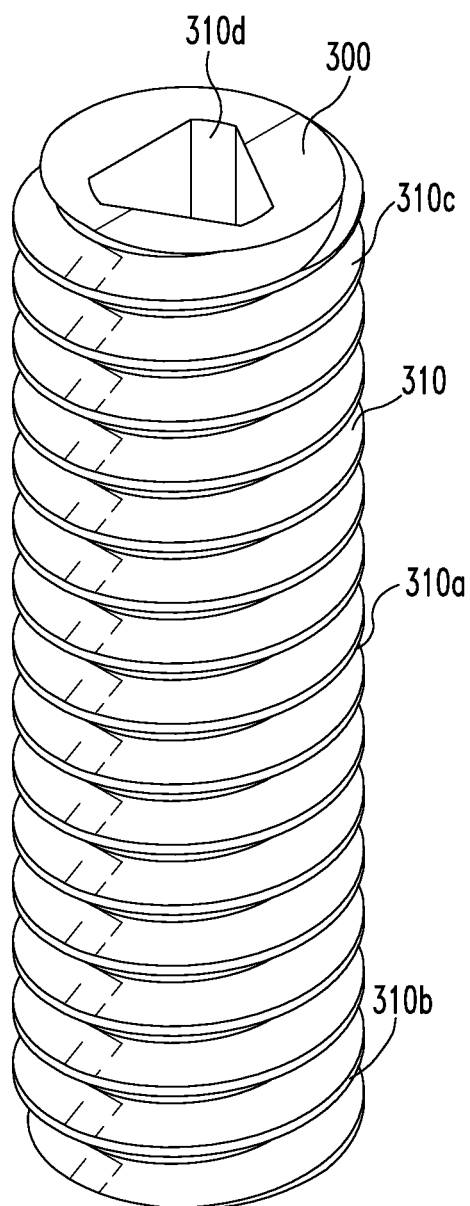
FIG. 11 shows a side elevational view of the insertion member of the anchor assembly FIG. 8.
Figure 12:
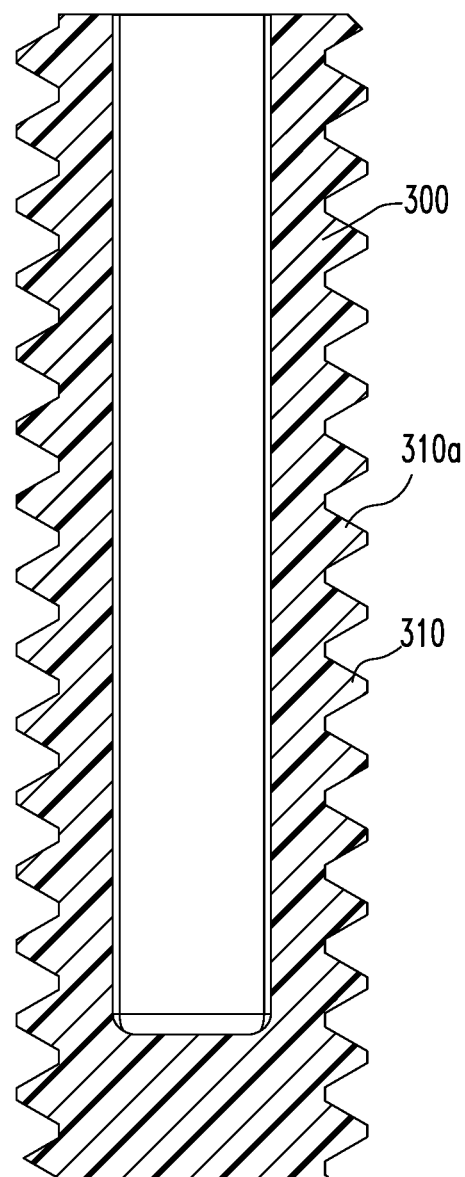
FIG. 12 shows a cross-sectional view of the insertion member of FIG. 11.
Figure 13:
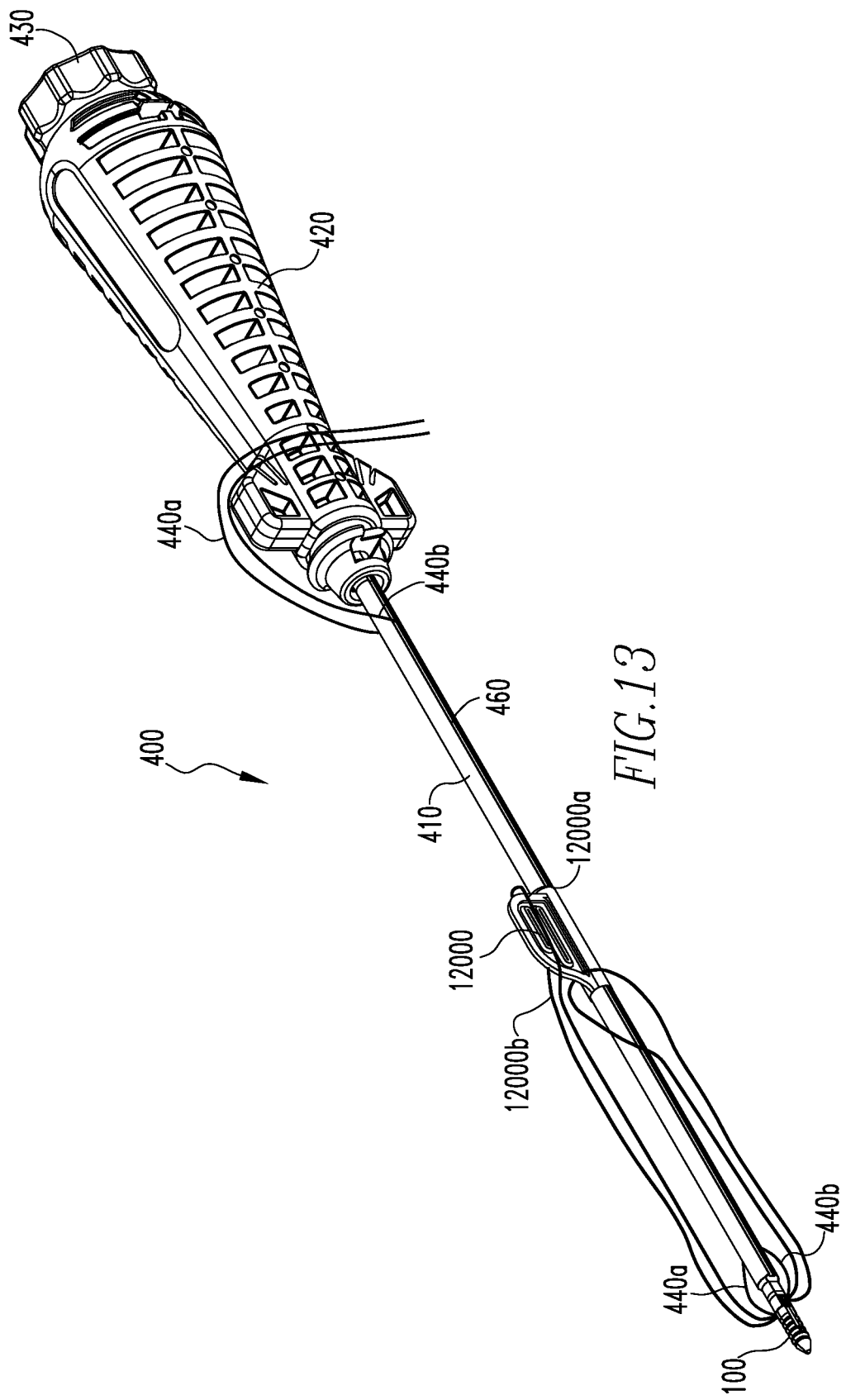
FIG. 13 shows an isometric view of the delivery device for use with the anchor assembly of FIG. 8.

The insertion member 300 includes a body 310 having threads 310a, a distal portion 310b, and a proximal portion 310c. As shown in FIGS. 8, 11, and 12, the member 300 includes a triangular-shaped cannulation 310d that extends a partial length of the member 300. The threads 310a are configured for engagement with the threads 230c of the cavity 230 when the insertion member 300 is arranged within the cavity 230, as will be further explained below.

FIGS. 13-14, 14A-14B, 15, and 15A-15B show the delivery device 400 of the present disclosure for use with the anchor assembly 100 of FIG. 8. The device 400 includes a shaft 410, a handle 420 coupled to the shaft 410, and a knob 430 coupled to the handle 420. The shaft 410 includes an outer member 410a and an inner member 410b slidably disposed within and coupled to the outer member 410a. The inner member 410b includes a distal end 410b' configured for disposal within the cannulation 310d of the insertion member 300 and a proximal end 410b" coupled to the knob 430. The end 410b' is of a diameter such that it engages the wall 310d' of the cannulation 310d, thereby allowing movement of the member 30 when the knob 430 is rotated, as will be further described below. The outer member 410a includes prongs 410c located at a distal end 410a' of the outer member 410a and a proximal end 410a" coupled to the handle 420.

Prior to use, suture 440 is disposed within the through hole 250 and ends 440a,440b of the suture 440 are fixed to suture holders 450 located on handle 420. The suture 440 helps to keep anchor 200 coupled to the shaft 410. The delivery device 400 and its components, especially the knob 430, is similar to the delivery device shown and described in the '869 publication. The ends 440a,440b of the suture 440 are also housed within channels 460 that extend along the shaft 410. A suture threader 12000 is also releasably coupled to the shaft 410. Threader 12000 includes a clip 12000a and a loop of suture 12000b coupled to the clip 12000a. Suture loop 12000b is disposed within the through hole 250 and placed around the clip 12000a.

As shown in FIGS. 14A and 15A, the prongs 410c are disposed within the depressions 260. Once the anchor assembly 100 is disposed within bone, the prongs 410c help to hold the anchor 200 stationary while the insertion member 300 is moved relative to the anchor 200 via rotation of the knob 430. As will be further described below, FIG. 14A shows the location of the insertion member 300 prior to fixation of suture within the through hole 250, while FIG. 15A shows the location of the insertion member 300 after fixation of suture within the through hole 250.

Figure 14B:
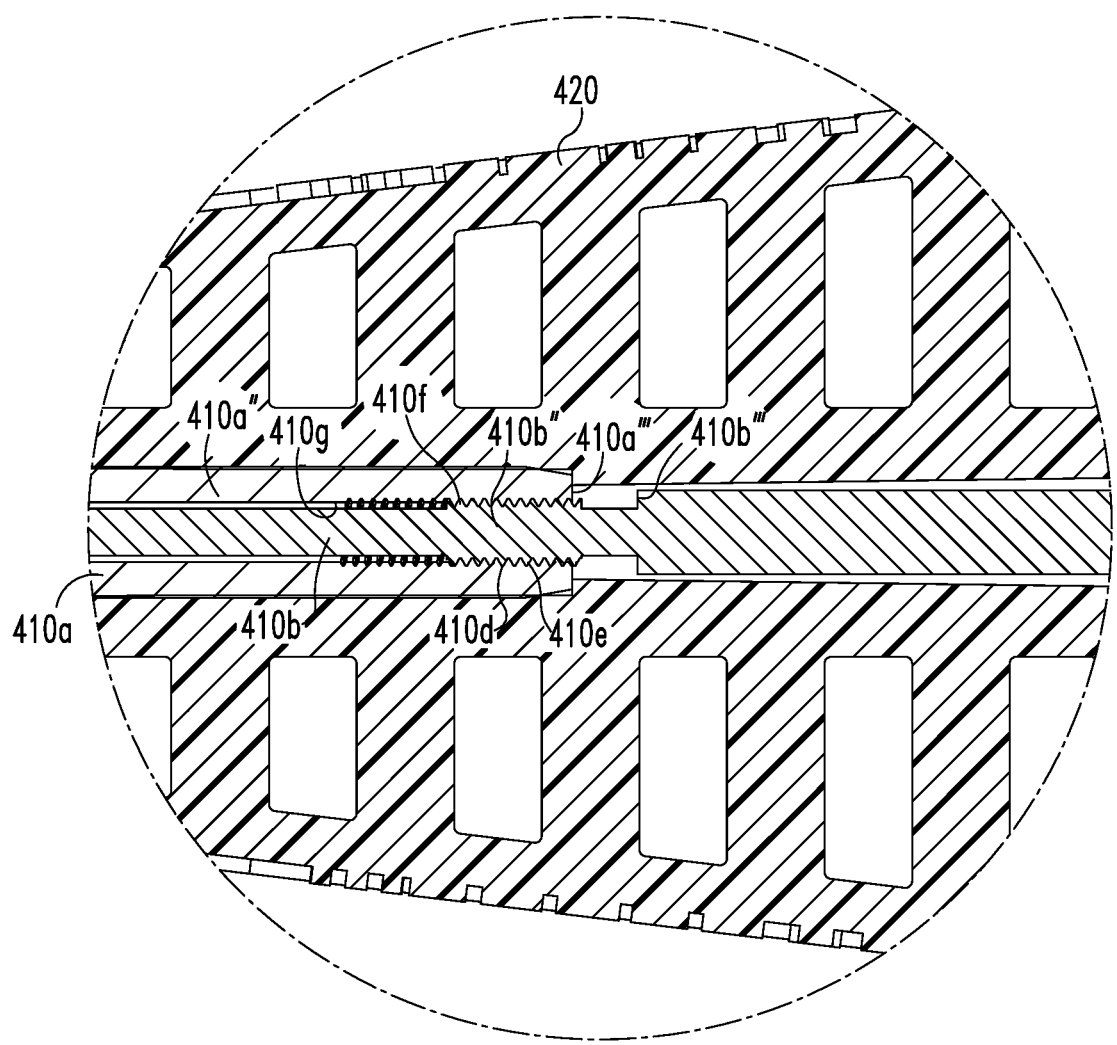
FIG. 14B shows an exploded view of the proximal ends of the outer and inner members of the delivery device of FIG. 14.
Figure 15B:
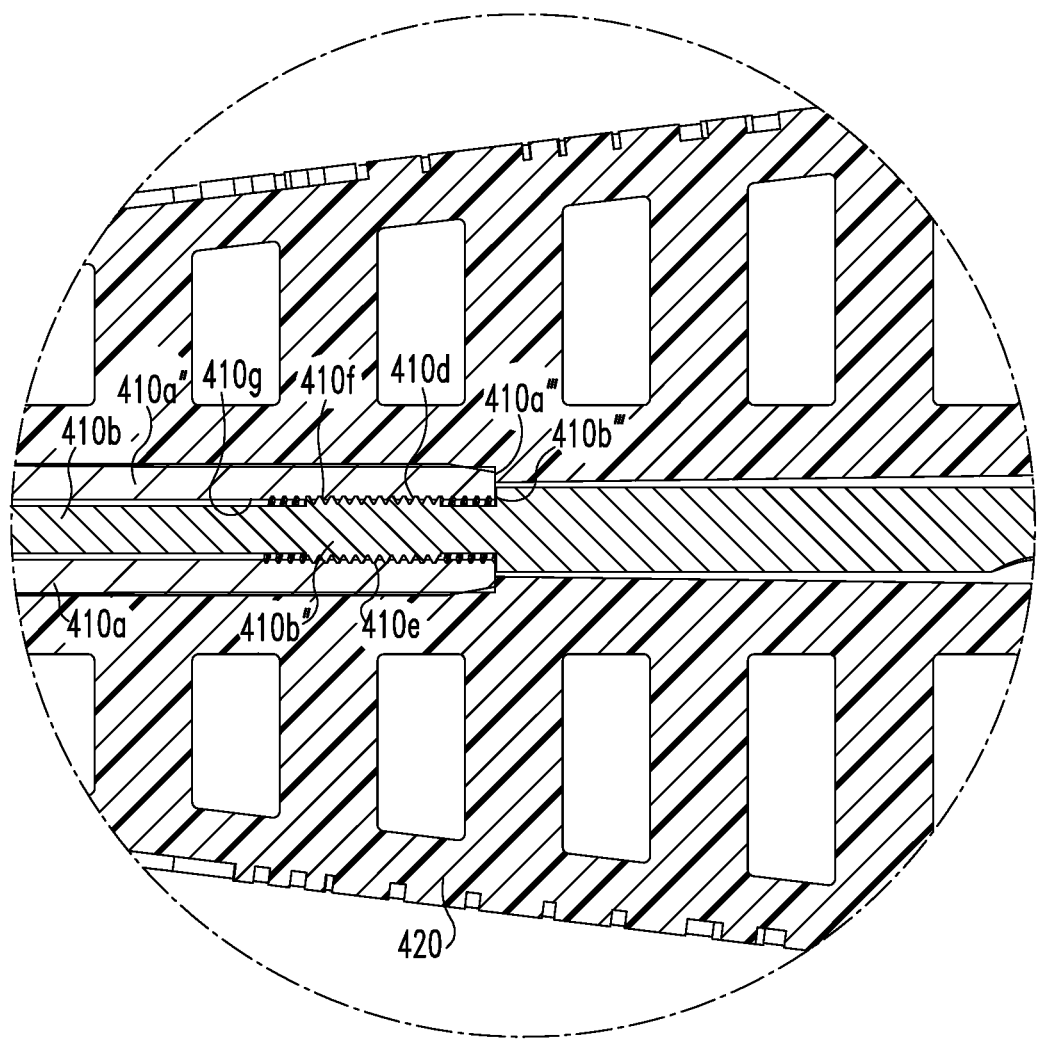
FIG. 15B shows an exploded view of the proximal ends of the outer and inner members of the delivery device of FIG. 14.

Additionally, as shown in FIGS. 14B and 15B, the proximal end 410b" of the inner member 410b includes threads 410d on an outer surface 410e of the inner member 410b and the proximal end 410a" of the outer member 410a includes threads 410f on an inner surface 410g of the outer member 410a. Threads 410f engage threads 410d to allow for coupling of the outer and inner members 410a, 410b and axial movement of the inner member 410b relative to the outer member 410a. Axial movement of the inner member 410b relative to the outer member 410a allows for axial movement of the insertion member 300 to the two locations shown in FIGS. 14A and 15A. Member 410b also includes a depth stop 410b''' that engages an end 410a''' of member 410a, as shown in FIG. 15B, once member 300 is located as shown in FIG. 15A. Interaction of the depth stop 410b''' with the end 410a''' ceases axial movement of the member 300 toward the through hole 250 and prevents the member 300 from being overly inserted into the cavity 230. The insertion member 300 is moved axially towards the through hole 250 to engage the flexible member and secure the flexible member within the cavity 230, which will be further described below.

Figure 16:
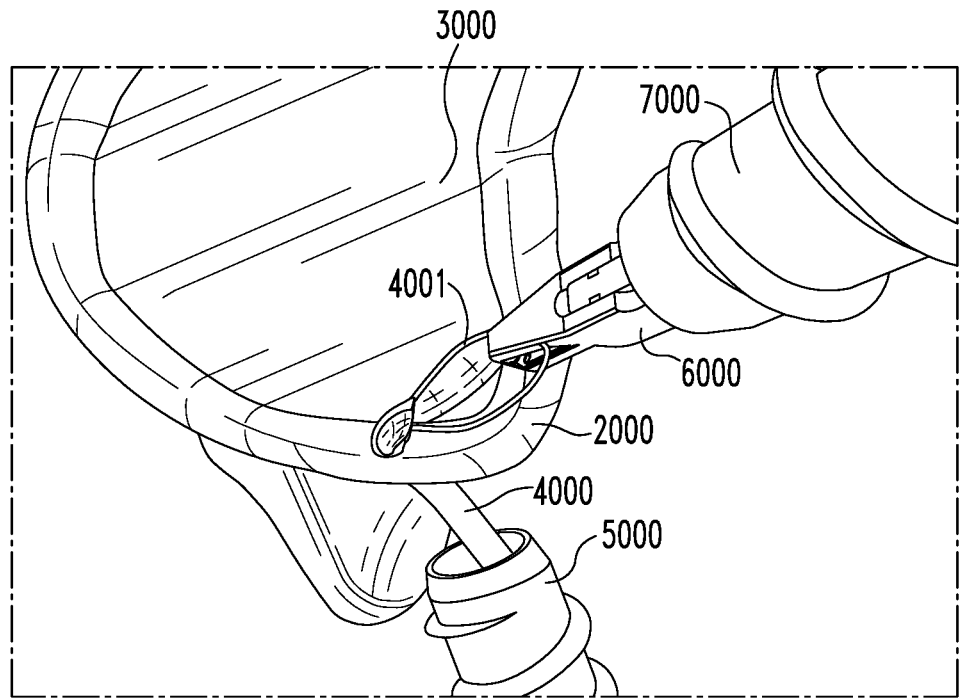
FIGS. 16-27 show a method of tissue repair via use of the delivery device and anchor assembly of FIGS. 1 and 13.
Figure 17:
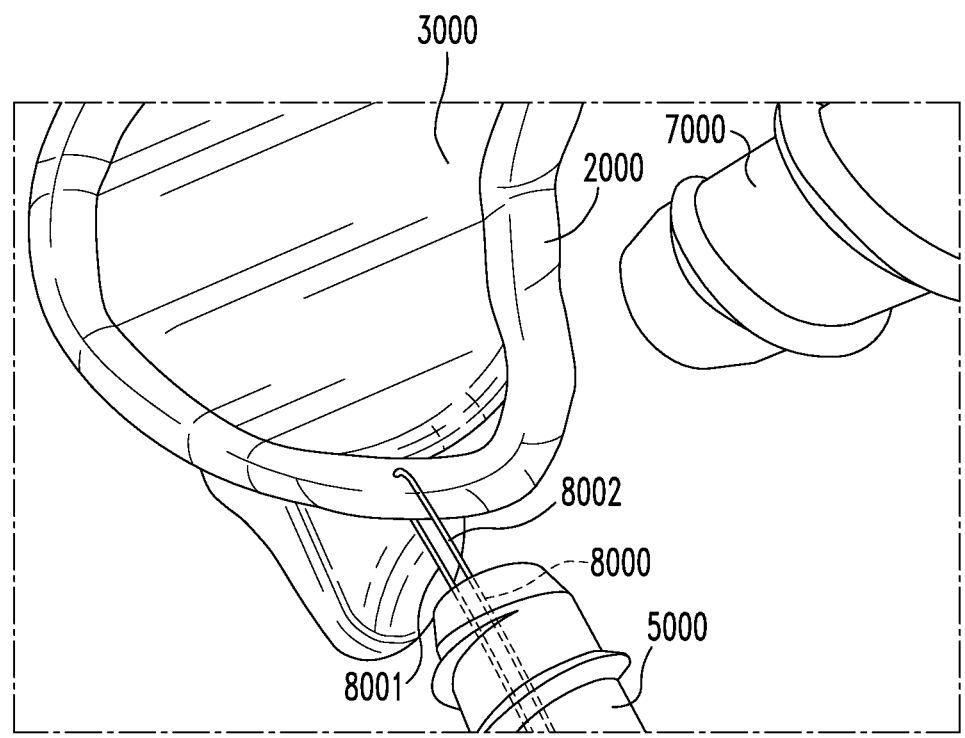

FIGS. 16-27 show the anchor assembly 10,100 of the present disclosure in use during soft tissue repair, specifically to repair labrum tears in the shoulder. As shown in FIG. 16, the labrum 2000 has been torn away from the glenoid cavity 3000 and is in need of being re-attached. FIG. 16 shows a monofilament suture loop 4001 from a suture passer 4000 being inserted through the labrum 2000 via use of a first cannula 5000. A grasper 6000 from a second cannula 7000 grabs the loop 4001 and pulls it through the second cannula 7000. Once the loop 4001 is pulled through the second cannula 7000, one end 8001 of a suture 8000 is passed through the loop 4001. The one end 8001 of the suture 8000 is pulled through the labrum 2000 and first cannula 5000 via the loop 4001, while the other end 8002 is grasped and pulled through the first cannula 5000 to have both ends 8001,8002 exiting the cannula 5000, as shown in FIG. 17.

Figure 18:
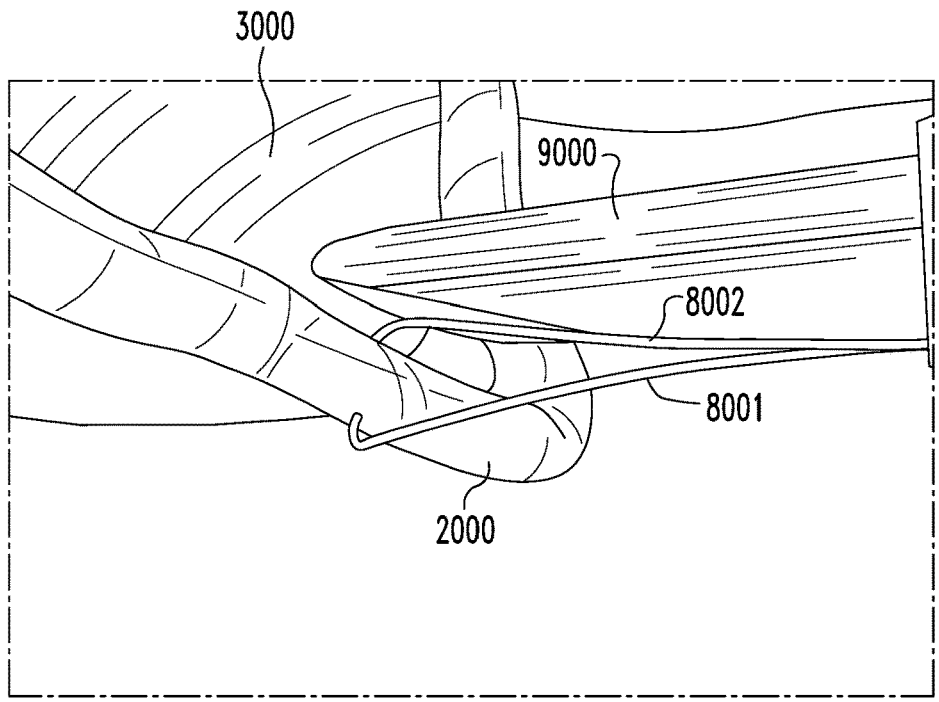
Figure 19:
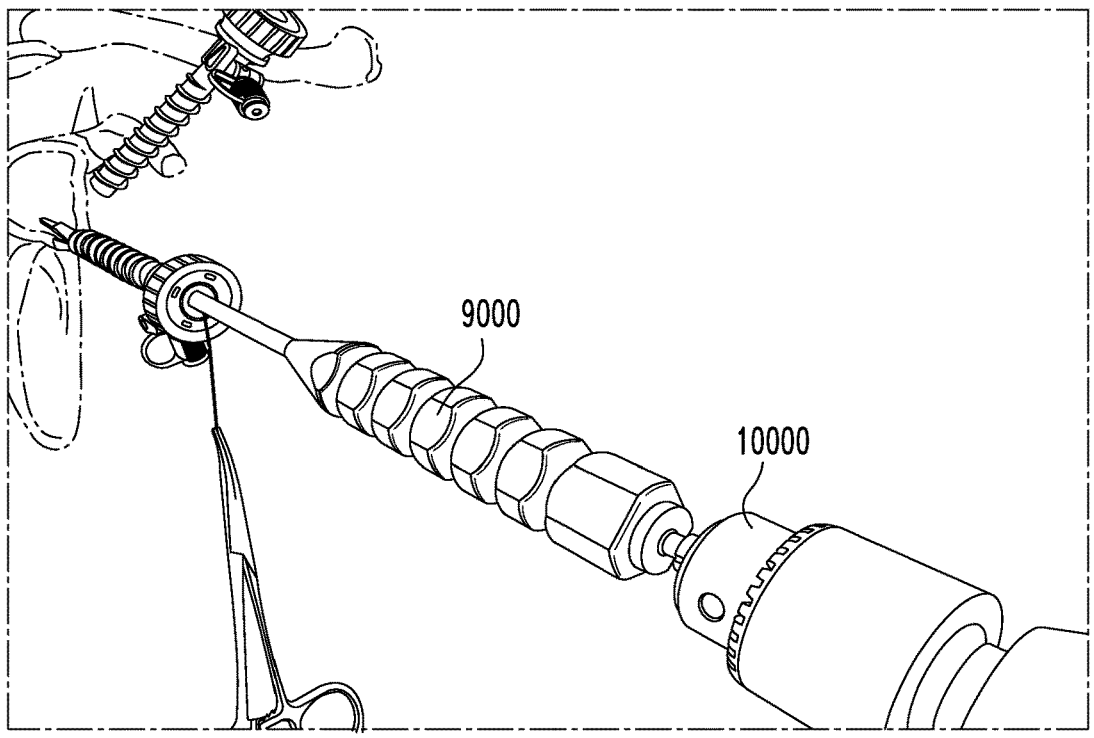
Figure 20:
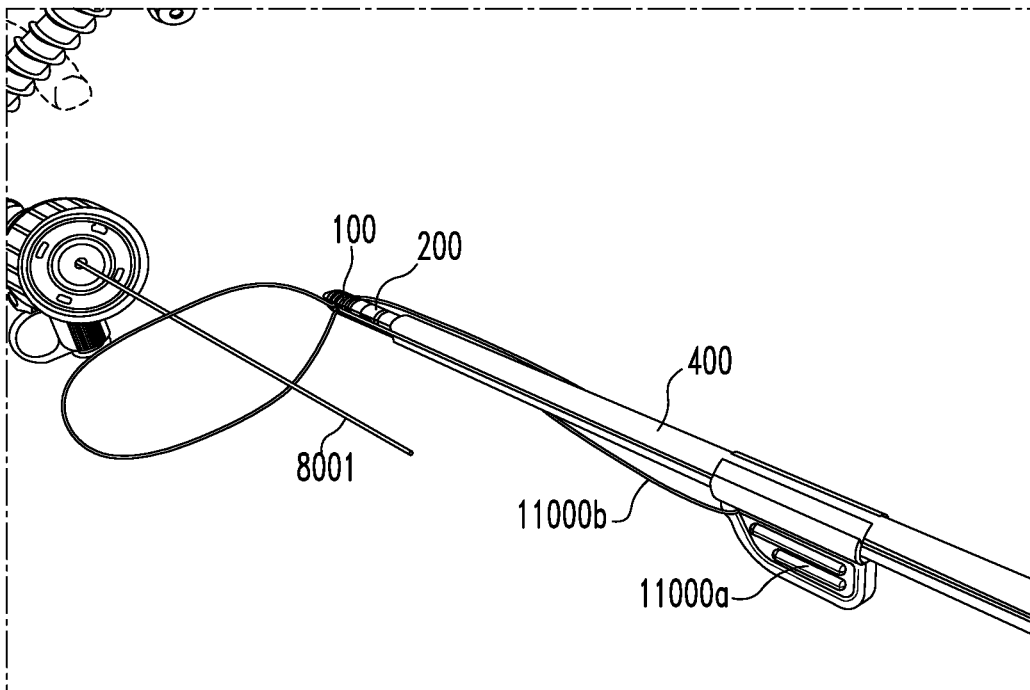
Figure 21:
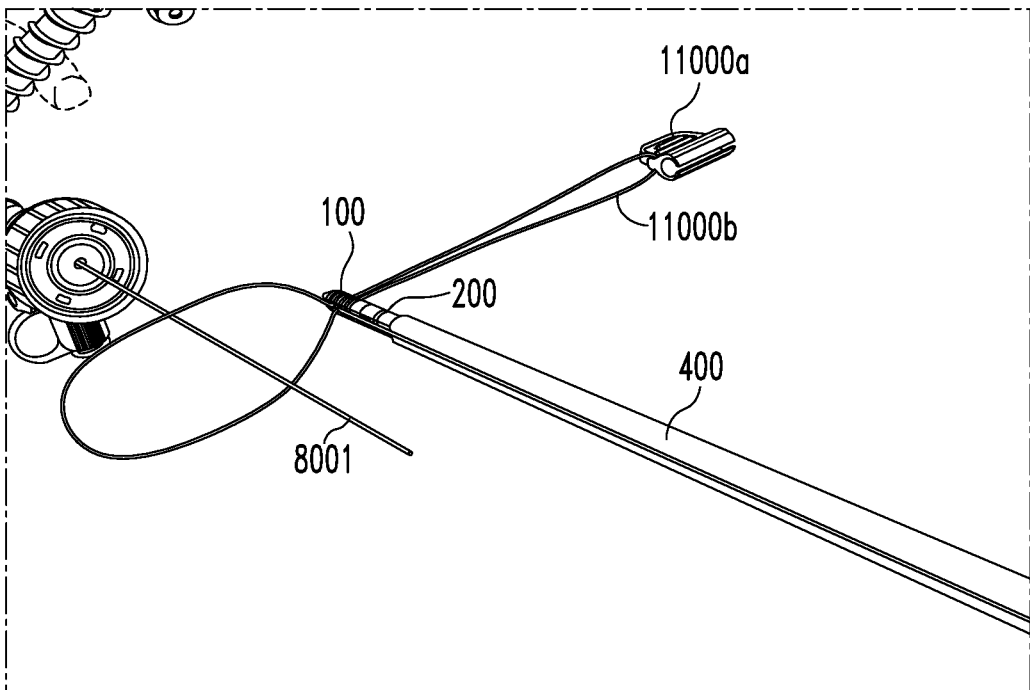
Figure 22:
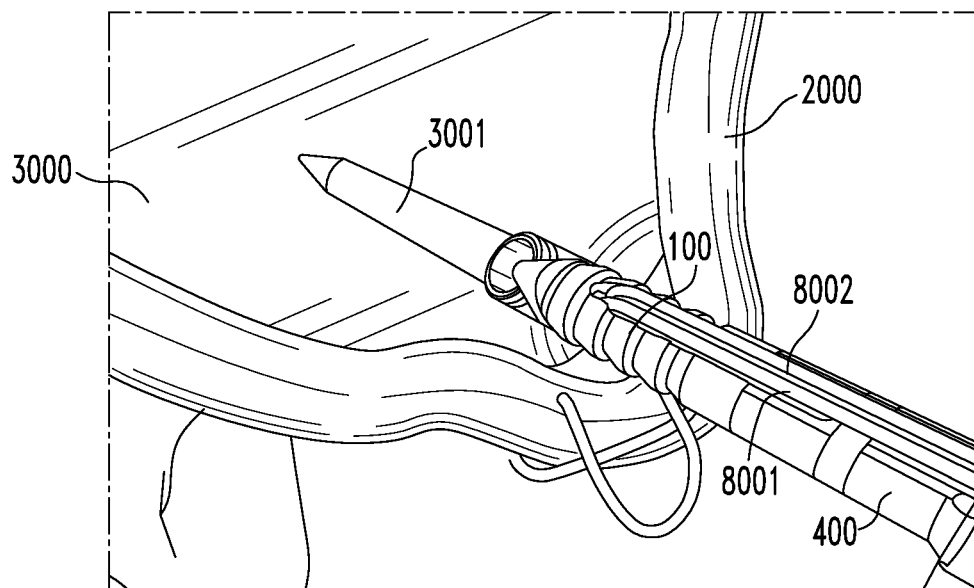
Figure 23:
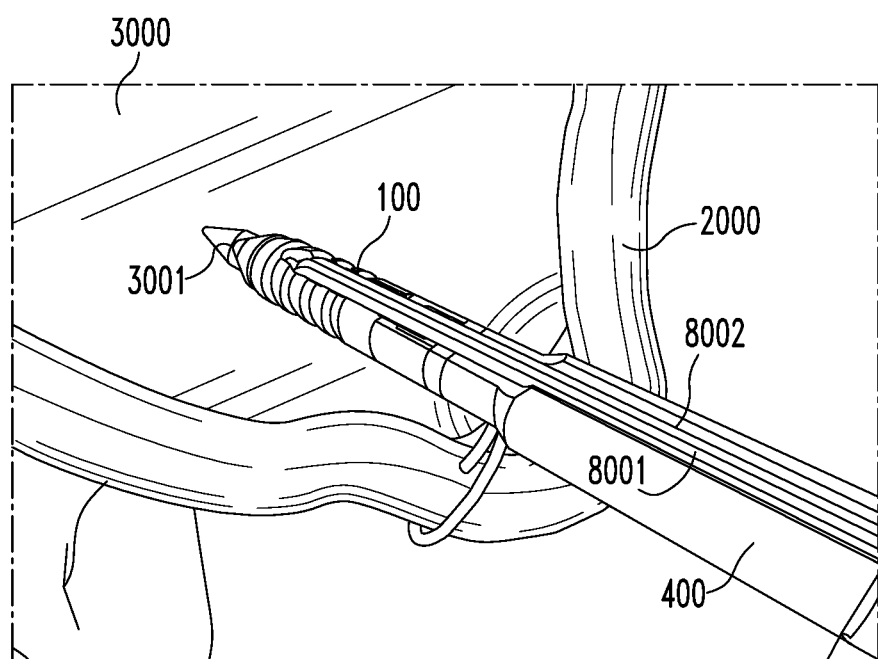
Figure 24:
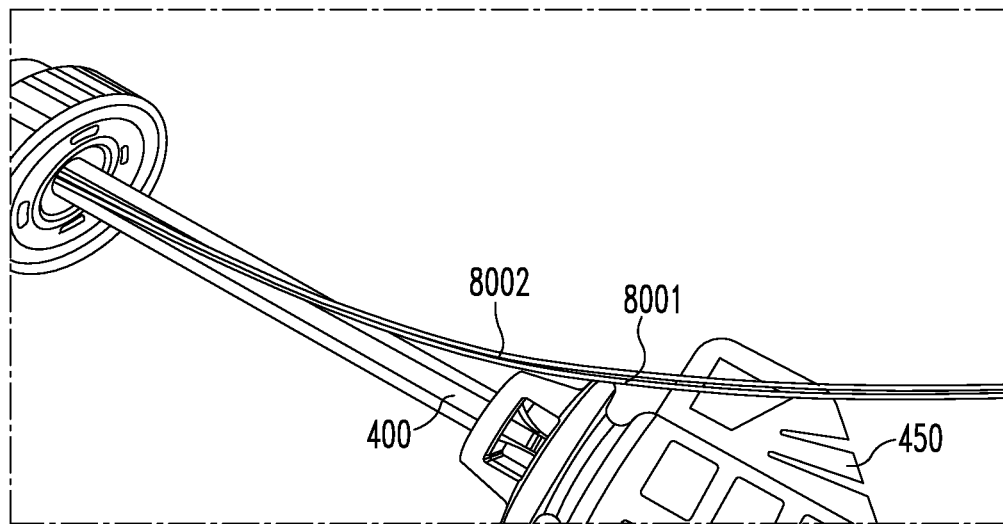
Figure 25:
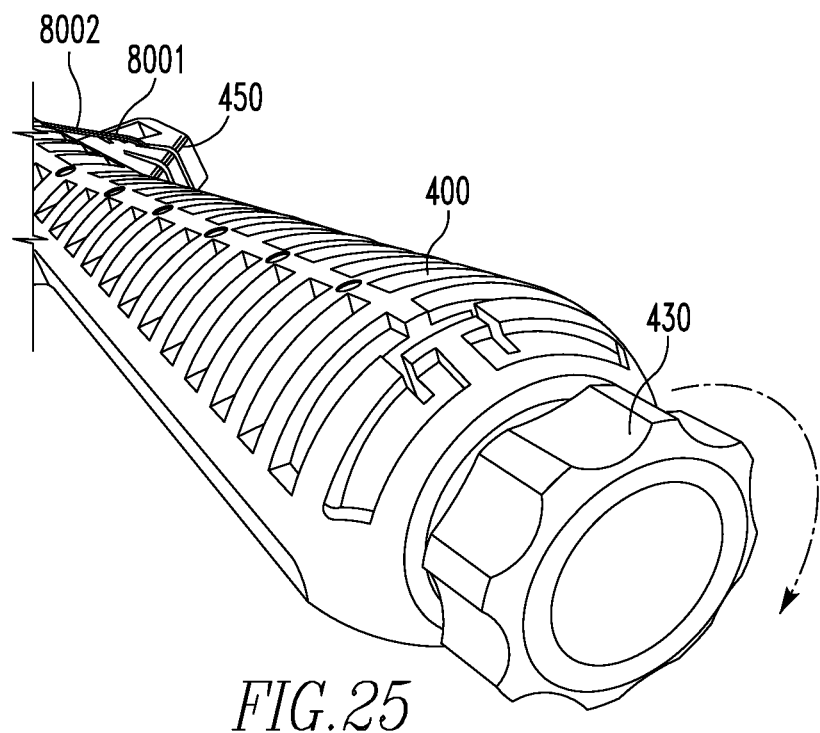

A hole 3001 is then made in the glenoid 3000 via the use of a drill guide 9000 and drill 10000, as shown in FIGS. 18 and 19. The ends 8001,8002 are placed through the suture threader loop 11000b,12000b and pulled through the through hole 25,250 of the anchor 20,200, as shown in FIGS. 20 and 21. The suture 44,440 is removed from the delivery device 40,400 prior to inserting the anchor assembly 10,100 into the hole 3001. After the anchor assembly 10,100 is inserted into the hole 3001, as shown in FIGS. 22 and 23, the suture ends 8001,8002 are tensioned and the ends 8001,8002 are locked by placing the ends 8001,8002 in the suture holder 45,450, as shown in FIG. 24, and the inner plug 30,300 is then rotated, via rotation of the knob 43,430 to fixate the suture 8000 in the cavity 23,230.

Figure 26:
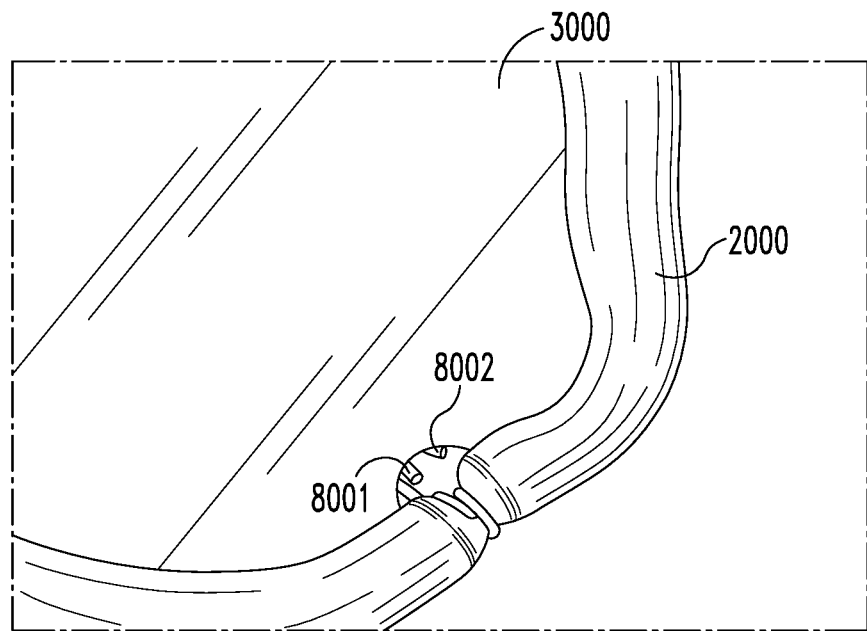
Figure 27:
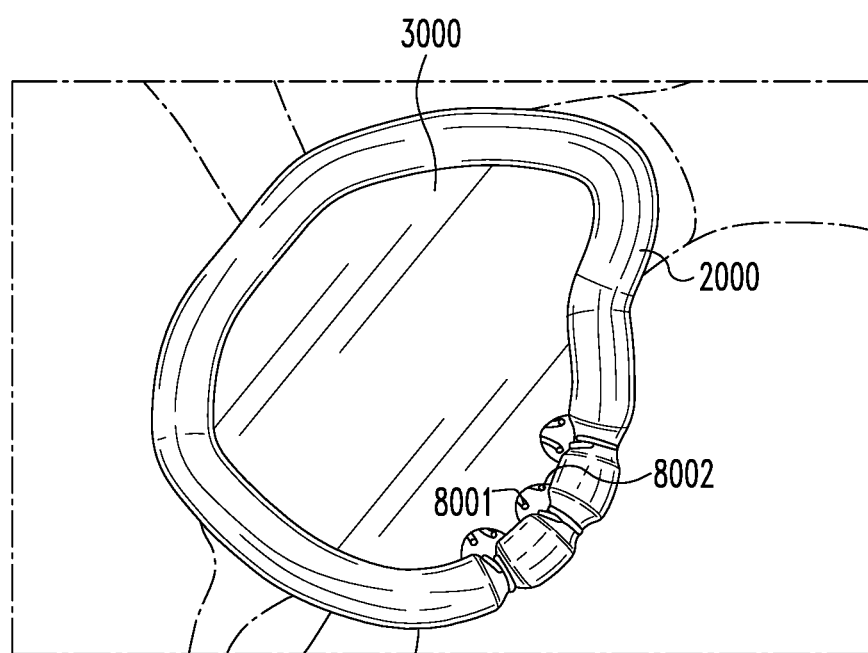

The suture ends 8001,8002 are cut, as shown in FIG. 26, and the delivery device 40,400 is removed. Additional anchor assemblies 10,100 may be inserted until the desired final repair is completed, as shown in FIG. 27. For clarity purposes, only end 8001, suture loop 12000b, and anchor assembly 100 are shown in FIGS. 20-23. However, in practice, both ends 8001,8002 are used and suture loop 11000b and anchor assembly 10 may be used rather than suture loop 12000b and anchor assembly 100.

FIGS. 28-33 show an alternative embodiment of the anchor assembly 500 of the present disclosure and its components. The assembly 500 includes the anchor 600 and the insertion member 700. The anchor 600 includes a proximal portion 610, a distal portion 620, and an inner cavity 630. The inner cavity 630 will be further described below. An opening 640 to the cavity 630 is located at the proximal portion 610 of the anchor 600. The anchor 600 also includes a transverse hole 650 extending through the anchor 600. The through hole 650 is for housing of a flexible member, such as suture. Openings 650a,b are located at each end of the through hole 650. The outer surface 670 of the proximal portion 610 also includes wings 680 for substantially reducing the possibility of removal of the anchor 600 when inserted into bone. The wings 680 are unlike barbs 28,280 in that wings 680 are longer, have more space between them, and extend further upward and outward then barbs 28,280. The outer surface 670 also includes at least two slots 690 extending from the openings 650a,b of the through hole 650. The slots 690 intersect the wings 680 and are configured for housing of the suture after positioning of the anchor 600 in bone. As shown in FIG. 10, the cavity 630 extends into and beyond the through hole 650 and includes a non-threaded proximal portion 630a and a threaded distal portion 630b. The proximal portion 630a is square-shaped to correspond with an end of the delivery device used to insert the anchor 600 into bone, as will be further described below. The proximal portion 630a also has a larger diameter and is shorter than the distal portion 630b.

The insertion member 700 includes a body 710 having a threaded proximal portion 710a and a non-threaded distal portion 710b. The proximal portion 710a has a larger diameter than the distal portion 710b. The member 700 includes a triangular-shaped cannulation 710e that extends a partial length of the member 700. The threads 710a' are configured for engagement with the threads 630c of the cavity 630 when the insertion member 700 is arranged within the cavity 630, as will be further explained below.

FIGS. 34, 34A, 35, 35, 36, 36A-36B, and 37A-37B show the delivery device 800 of the present disclosure. The device 800 includes a shaft 810, a handle 820 coupled to the shaft 810, and a knob 830 coupled to the handle 820. The shaft 810 includes an outer member 810a and an inner member 810b slidably disposed within and coupled to the outer member 810a. The inner member 810b includes a distal end 810b' configured for disposal within the cannulation 710e of the insertion member 700 and a proximal end 810b" coupled to the knob 830. The end 810b' is of a diameter such that it engages the wall 710e' of the cannulation 710e, thereby allowing movement of the member 700 when the knob 830 is rotated, as will be further described below. The outer member 810a includes a square-shaped tip 810c extending from a distal end 810a' of the outer member 810a and a proximal end 810a" coupled to the handle 820.

The handle 820 includes suture holders 850, each suture holder 850 extending from a side of the handle 820. Additionally, as shown in FIG. 34, a flexible member 900, such as a suture, is housed within the through hole 650 with each end 900a,900b of the member 900 being coupled to a holder 850. The flexible member 850 helps to hold the anchor 600 on the device 800 prior to insertion of the anchor 600 into bone. The ends 900a,900b of the suture 900 are also housed within channels 860 that extend along the shaft 810. A suture threader 13000 is also releasably coupled to the shaft 81. Threader 13000 includes a clip 13000a and a loop of suture 13000b coupled to the clip 13000a. Suture loop 13000b is disposed within the through hole 650 and placed around the clip 13000a. The delivery device 800 and its components, especially the knob 830, are similar to the delivery device shown and described in the '869 publication.

As shown in FIGS. 36 and 37, the tip 810c is disposed within the proximal portion 630a. Once the anchor assembly 500 is disposed within bone, the tip 810c helps to hold the anchor 600 stationary while the insertion member 700 is moved relative to the anchor 600. Additionally, as shown in FIG. 14A, the proximal end 810b'' of the inner member 810b includes threads 810d on an outer surface 810e of the inner member 810b and the proximal end 810a'' of the outer member 810a includes threads 810f on an inner surface 810g of the outer member 810a. Threads 810f engage threads 810d to allow for coupling of the outer and inner members 810a, 810b and axial movement of the inner member 810b relative to the outer member 810a.

Figure 36B:
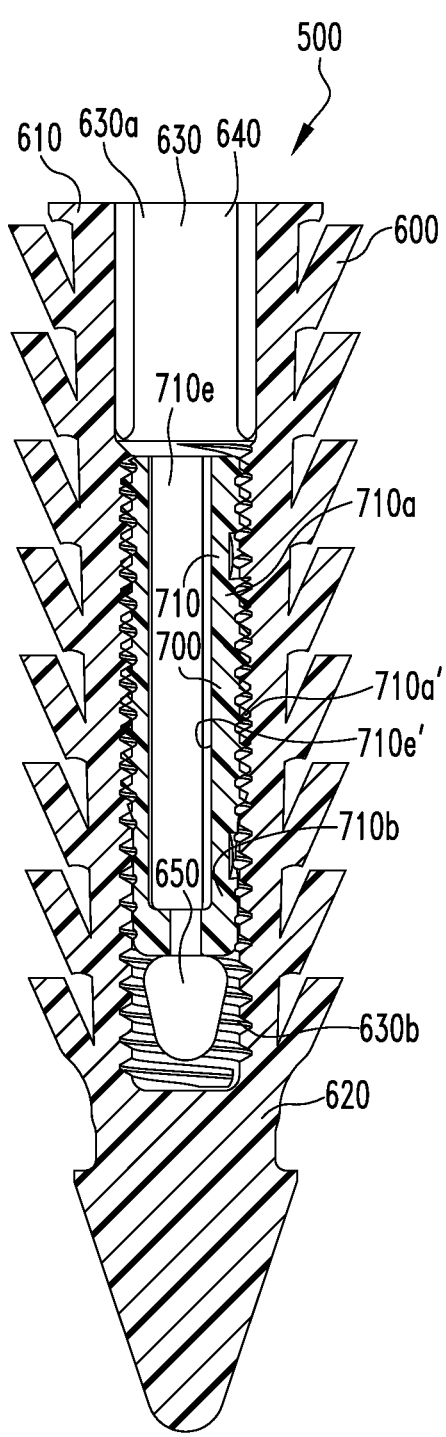
FIG. 36B shows an exploded view of the anchor assembly of FIG. 36.
Figure 37B:
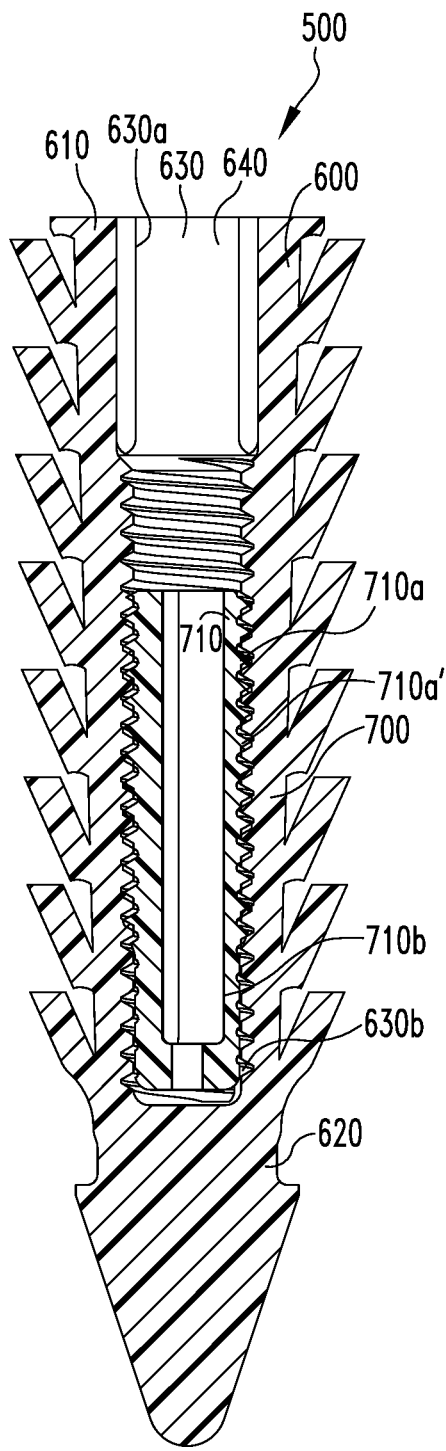
FIG. 37B shows an exploded view of the anchor assembly of FIG. 37.

Axial movement of the inner member 810b relative to the outer member 810a allows for axial movement of the insertion member 700 to the two locations shown in FIGS. 36B and 37B. Member 810b also includes a depth stop 810b''' that engages an end 810a''' of member 810a, as shown in FIG. 37A, once member 700 is located as shown in FIG. 37B. Interaction of the depth stop 810b'' with the end 810a''' ceases axial movement of the member 700 toward the through hole 650 and prevents the member 700 from being overly inserted into the cavity 630. The insertion member 700 is moved axially towards the through hole 650 to engage the flexible member and secure the flexible member within the cavity 630, which will be further described below.

During tissue repair via use of the anchor assembly 500 and the driver 800, suture from a previously placed anchor is pulled through the through hole 650. The manner in which the suture is pulled through the through hole 650 may be the same as the manner described in the '106 and '180 patent applications. The anchor assembly 500 is subsequently inserted into bone, via use of the driver 800, in the manner shown in FIG. 36B. Axial advancement of the anchor assembly 500 into the bone may occur via tapping on the handle 820. After the soft tissue is situated on the bone and the suture is located through the soft tissue, in the manner described in the '106 and '180 patent applications, the insertion member 700 is moved axially towards the distal portion 630b, via rotation of the knob 830 to engage the suture and secure the suture within the cavity 630, in the manner shown in FIG. 37B. For clarity purposes, only the anchor assembly 500 is shown in FIGS. 36B and 37B. However, a further description and showing of a method of tissue repair similar to the above-described method, is shown in the '106 and '180 published applications.

The components of the anchor assemblies 10,100,500 are made from a bioabsorbable polymer material via an injection molding process. However, other materials and processes may be used. In addition, the suture material is made from a bioabsorbable polymer material, but other material may be used. Furthermore, the outer surface 27, 270, 670 of the anchors 20,200,600 may include features other than barbs and wings 28,280,680 to reduce the possibility of removal of the anchor 20,200,600 and the barbs 28,280,680 may extend the entire length or a partial length of the anchor 20,200,600. Similarly, the body 31,310,710 of the insertion member 30,300,700 and the cavity 23,230,630 of the anchor 20,200,600 may include features other than threads to facilitate insertion and removal of the insertion member 30,300, 700 and the threads 31a',310a,710a' may extend the entire length or a partial length of the body 31,310,710 and cavity 23,230,630. Also, for the purposes of this disclosure, the through hole 25,250,650 may be located anywhere along the length of the anchor 20,200,600. Additionally, it is within the scope of this disclosure for the anchor 20,200,600 to have more or less than two slots 29,290,690.

Additionally, for the purposes of this disclosure, the outer member 41a410a includes at least one prong 41c,410c and the anchor 20,200 includes at least one corresponding depression 26,260. Also, the cannulation 31e,310e of the insertion member 30,300 may extend an entire length of the insertion member 30,300 and may include a shape other than triangular.

The outer and inner members 41a,41b,410a,410b,810a, 810b of the delivery device 40,400,800 include a stainless steel material, but may be made from any other metal or non-metal material that is bio-compatible and strong enough to withstand the forces that are placed on the members 41a,41b,410a,410b,810a,810b during surgery. The members 41a,41b,410a,410b810a,810b may be machined, die drawn and subsequently machined, or made by any other method known to one of skill in the art. The outer and inner members 41a, 41b,410a,410b,810a,810b are coupled to the handle 42,420,820 and knob 43,430,830 respectively, via a press-fit procedure. However, other methods of coupling the handle 42,420,820 and knob 43,430,830 to the members 41a,41b,410a,410b,810a,810b are also within the scope of this disclosure. The handle 42,420,820 and knob 43,430,830 are of a non-metal material, but may be made from a metal material, and both are made via an injection molding process. However, other methods of making are also within the scope of this disclosure.

Figure 38:
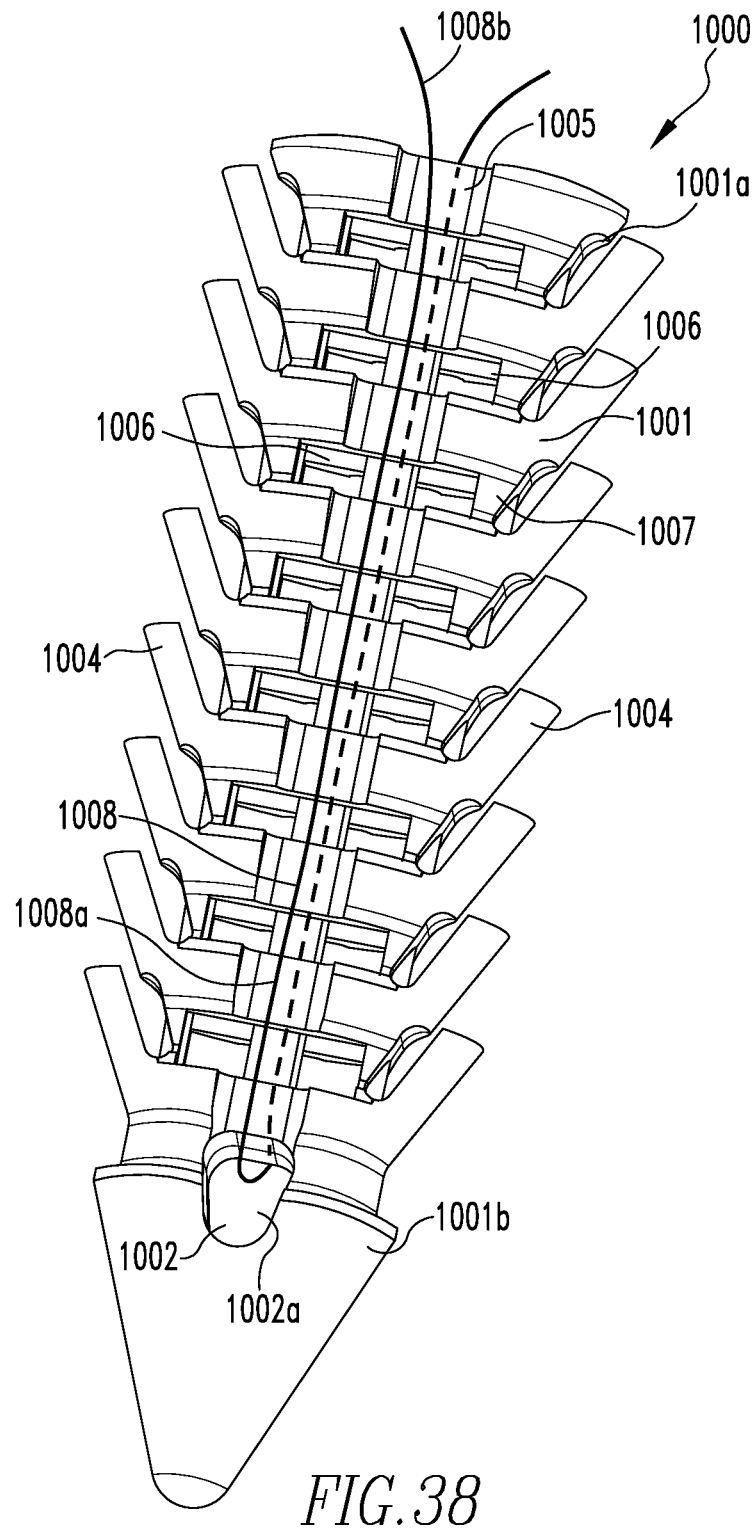
FIG. 38 shows an isometric view of a first embodiment of a fenestrated suture anchor of the present disclosure.
Figure 39:
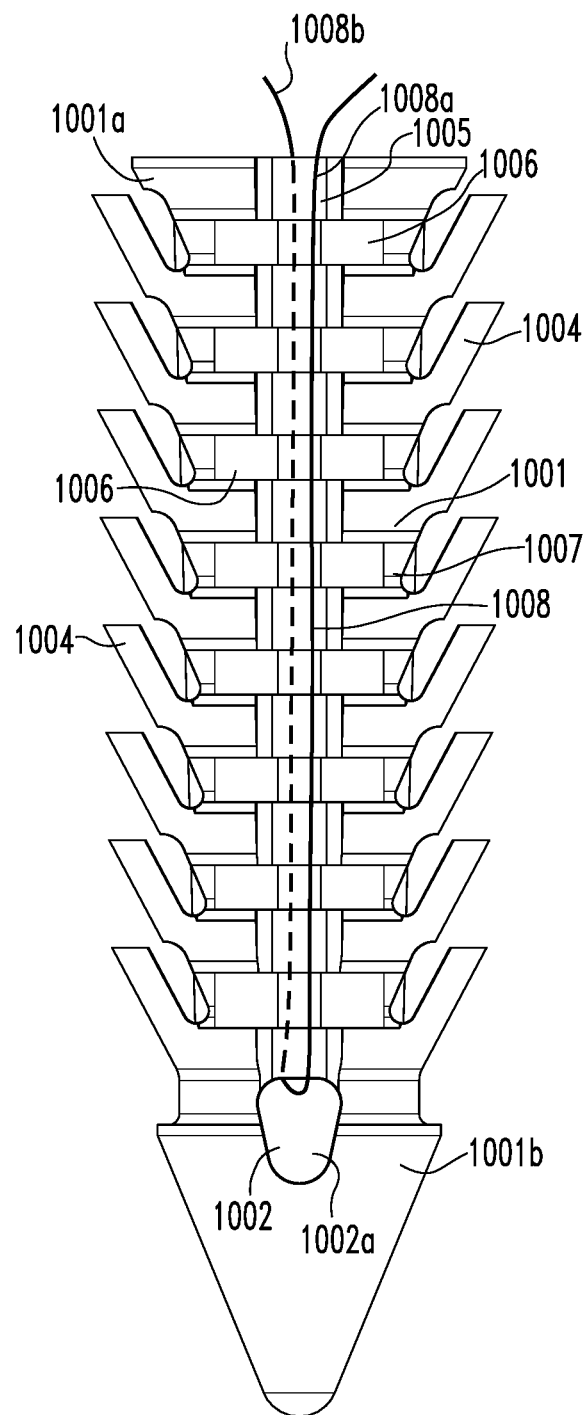
FIG. 39 shows a side view of the anchor of FIG. 38.
Figure 40:
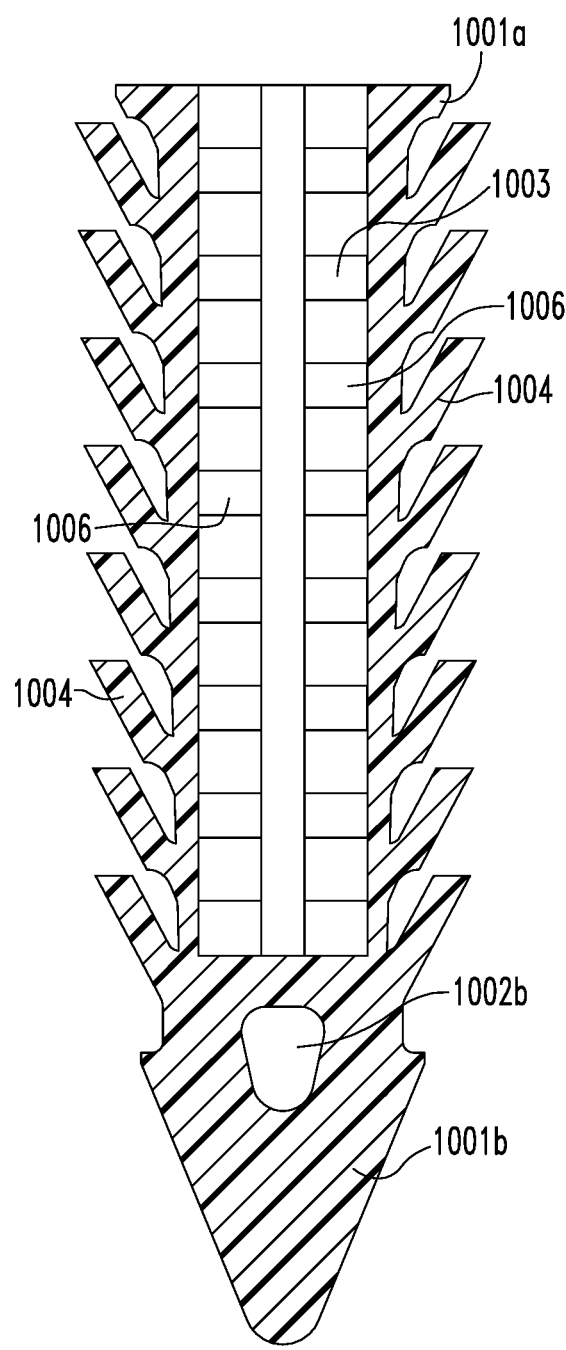
FIG. 40 shows a cross-sectional view of the anchor of FIG. 39.

FIGS. 38-40 show a first embodiment of a fenestrated suture anchor 1000 of the present disclosure. The anchor 1000 includes a body 1001 having a proximal portion 1001a and a distal portion 1001b, a transverse through hole 1002 located between the distal and proximal portions 1001b, 1001a, and a cavity 1003 extending a partial length of the body 1001. Wings 1004 exist along the body 1001 and outward from it. Similar to the wings 680, wings 1004 engage bone when the anchor 1000 is inserted into the bone, as will be further described below. The body 1001 also includes suture slots 1005 extending from openings 1002a, 1002b of the hole 1002. Additionally, there are channels 1006 extending along the body 1001 on both sides of the slots 1005. The channels 1006 extending from an outer surface 1007 of the anchor 1000 to the cavity 1003, thereby allowing the anchor 1000 to be fenestrated. The channels 1006 allow for ingrowth of tissue, such as bone, and other nutrients after insertion of the anchor 1000 into bone, as will be further described later. A suture 1008 is housed within the hole 1002 having its ends 1008a,1008b housed within the slots 1005.

Figure 41:
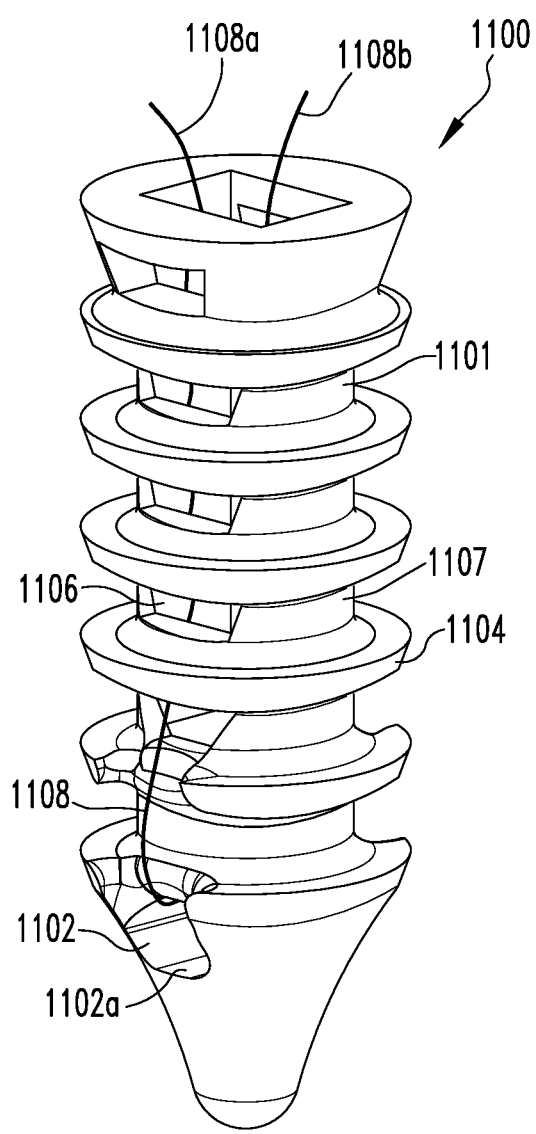
FIG. 41 shows a side elevational view of a second embodiment of a fenestrated suture anchor of the present disclosure.
Figure 42:
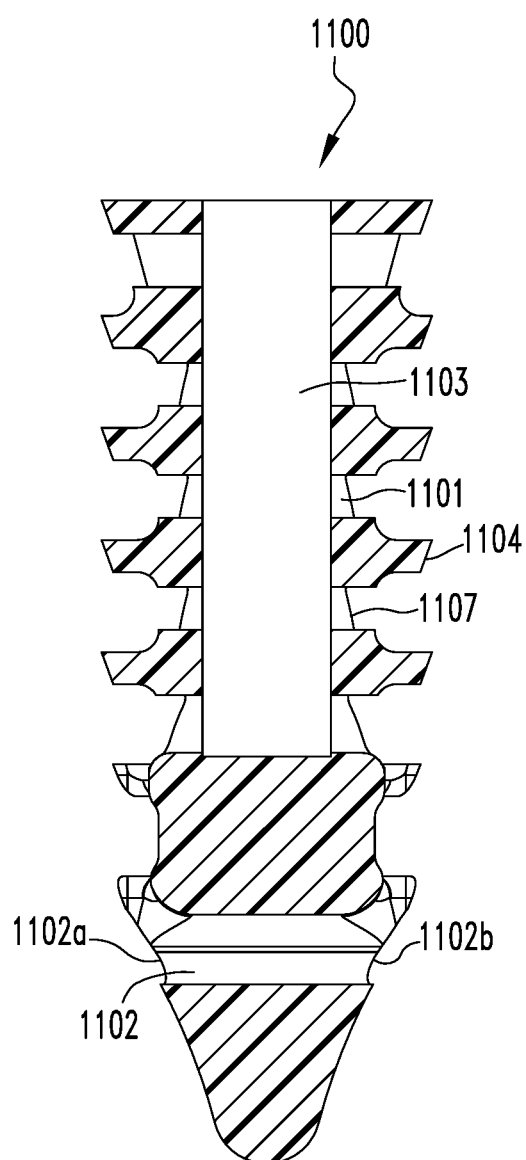
FIG. 42 shows a cross sectional view of the anchor of FIG. 41.

FIGS. 41-42 show a second embodiment of a fenestrated suture anchor 1100. The anchor 1100 includes a body 1101 having a proximal portion 1101a and a distal portion 1101b, a transverse through hole 1102 located between the distal and proximal portions 1101b,1101a, and a cavity 1103 extending a partial length of the body 1101. Barbs 1104 exist along the body 1101 and extend outward from it. Similar to the barbs 28,280, barbs 1104 engage bone when the anchor 1100 is inserted into the bone, as will be further described below. The body 1101 also includes channels 1106 extending along the body 1101. The channels 1106 extending from an outer surface 1107 of the anchor 1100 to the cavity 1103, thereby allowing the anchor 1100 to be fenestrated. The channels 1106 allow for ingrowth of tissue, such as bone, and other nutrients after insertion of the anchor 1100 into bone, as will be further described later. A suture 1108 is housed within the hole 1102 having its ends 1108a,1108b extend through openings 1102a,1102b and then back through the cavity 1103, as shown in FIG. 41.

Figure 43:
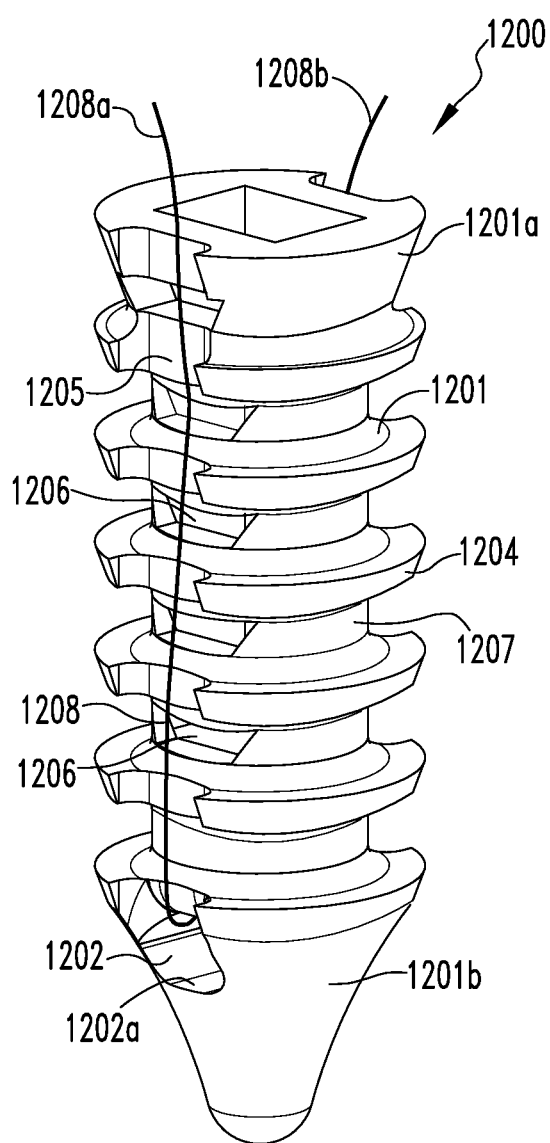
FIG. 43 shows a side elevational view of a third embodiment of a fenestrated suture anchor of the present disclosure.
Figure 44:
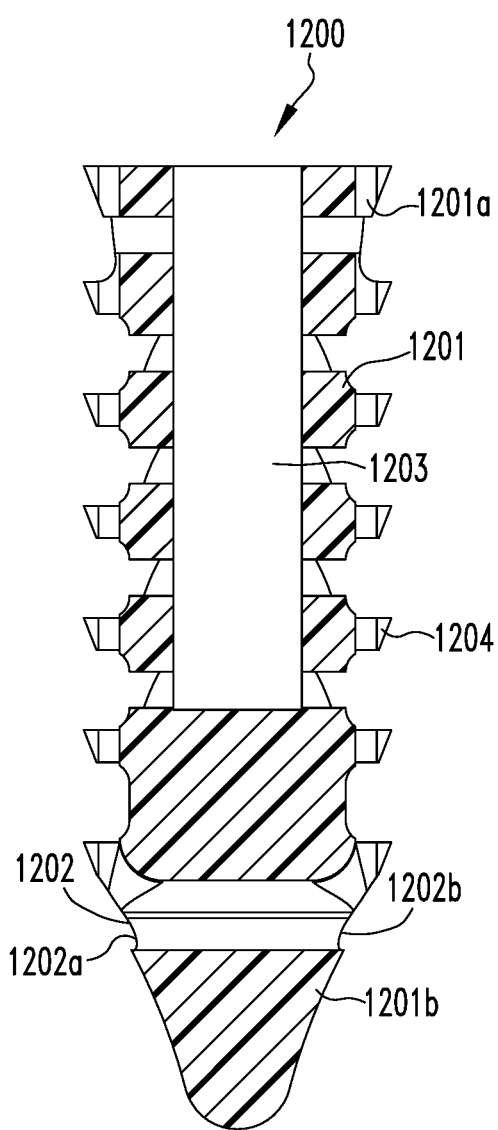
FIG. 44 shows a cross-sectional view of the anchor of FIG. 43.

FIGS. 43-44 show a first embodiment of a fenestrated suture anchor 1200 of the present disclosure. The anchor 1200 includes a body 1201 having a proximal portion 1201a and a distal portion 1201b, a transverse through hole 1202 located between the distal and proximal portions 1201b, 1201a, and a cavity 1203 extending a partial length of the body 1201. Barbs 1204 exist along the body 1201 and extend outward from it. Similar to the barbs 28,280, barbs 1204 engage bone when the anchor 1200 is inserted into the bone, as will be further described below. The body 1201 also includes suture slots 1205 extending from openings 1202a, 1202b of the hole 1202. Additionally, there are channels 1206 extending along the body 1201 interspaced with the slots 1205. The channels 1206 extend from an outer surface 1207 of the anchor 1200 to the cavity 1203, thereby allowing the anchor 1200 to be fenestrated. The channels 1206 allow for ingrowth of tissue, such as bone, and other nutrients after insertion of the anchor 1200 into bone, as will be further described later. A suture 1208 is housed within the hole 1202 having its ends 1208a,1208b housed within the slots 1205.

During repair of tissue via use of the suture anchors 1000,1100,1200, a delivery device having a handle and a shaft may be used to deliver the anchors into bone. An end of the shaft may be inserted into the cavity of the anchors and may have the same shape as cavity. The anchors 1000,1100,1200 are designed to be inserted into bone via axial motion. The torn tissue may then be placed on the bone, adjacent the anchors 1000,1100,1200. Subsequently, the suture may then be pulled through the tissue and tied to attach the tissue to the bone. A hole may be drilled in the bone prior to inserting the anchors 1000,1100,1200 into the bone.

Figure 28:
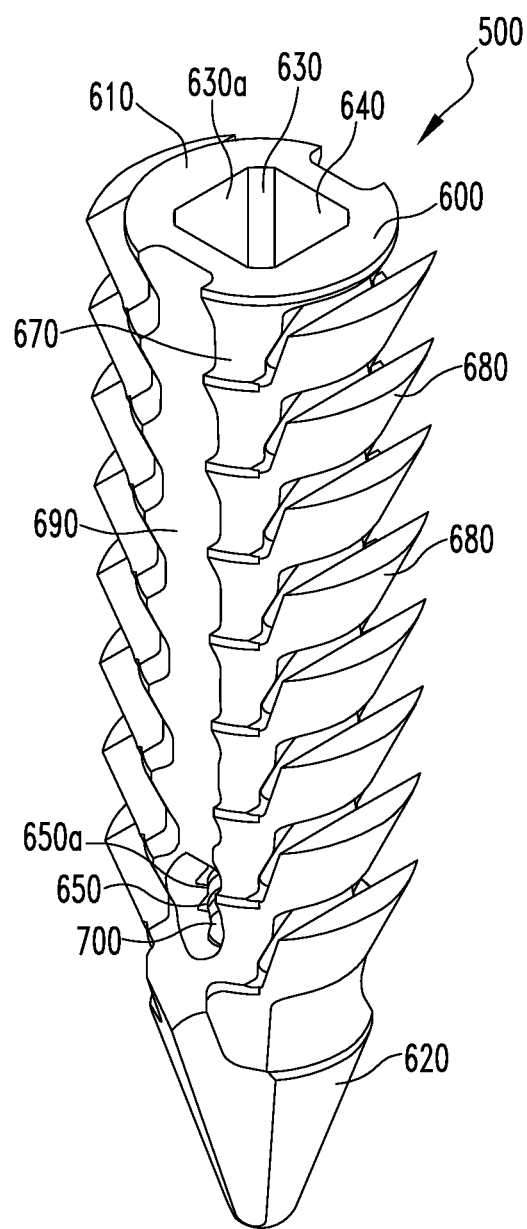
FIG. 28 shows a side elevational view of a third embodiment of the anchor assembly of the present disclosure.
Figure 29:
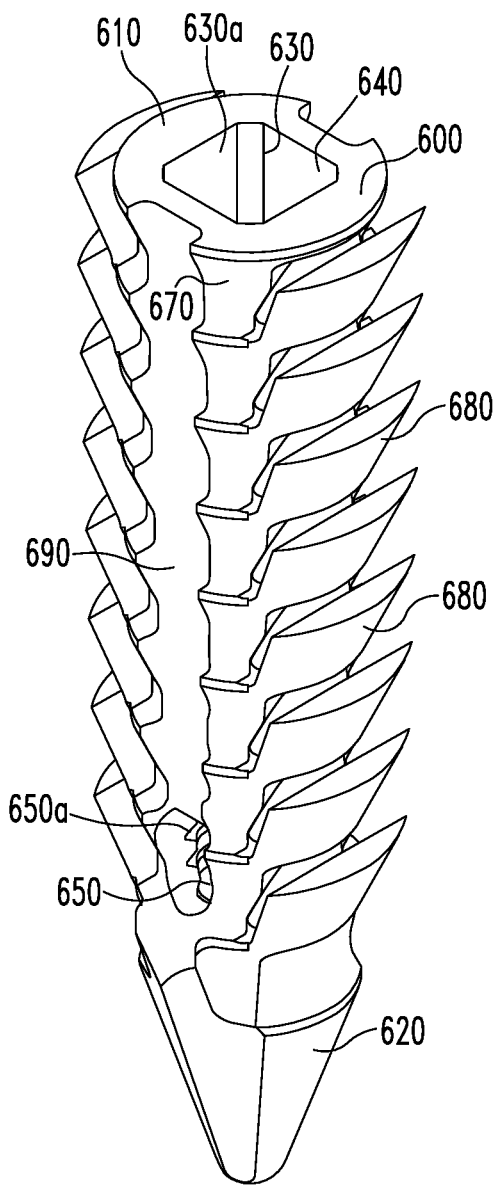
FIG. 29 shows a side elevational view of the anchor of the anchor assembly of FIG. 28.
Figure 30:
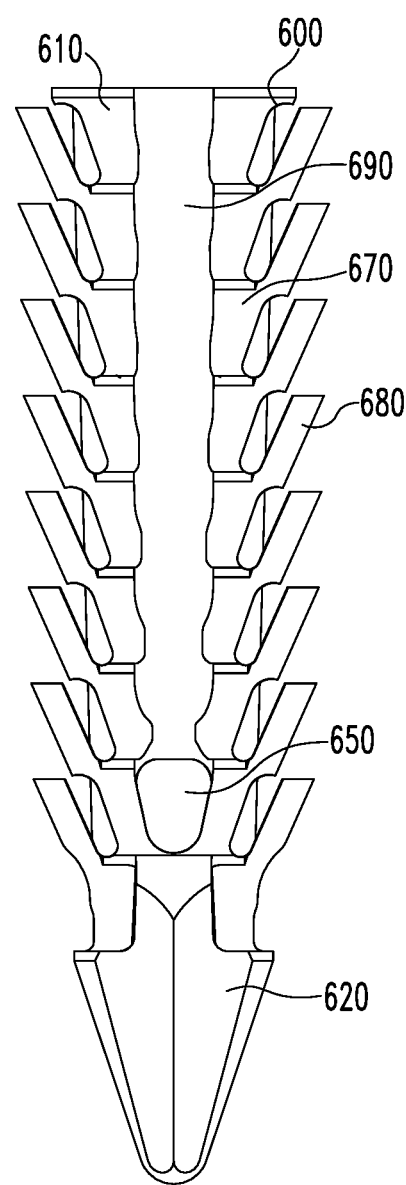
FIG. 30 shows a side view of the anchor of FIG. 29.
Figure 31:
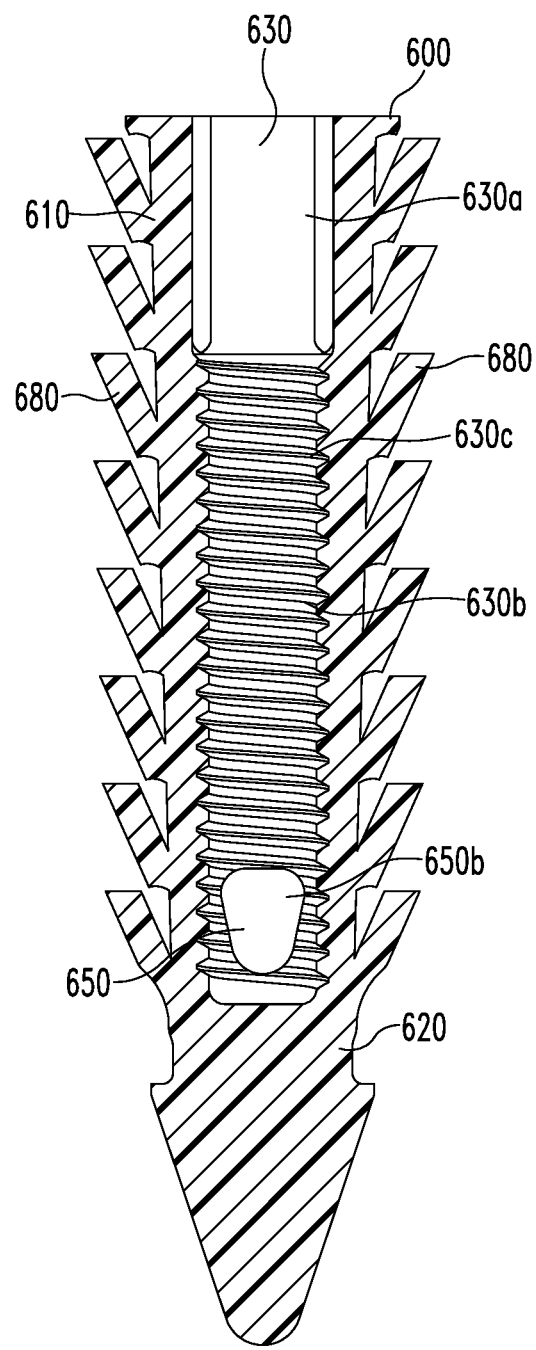
FIG. 31 shows a cross-sectional view of the anchor of FIG. 29.
Figure 32:
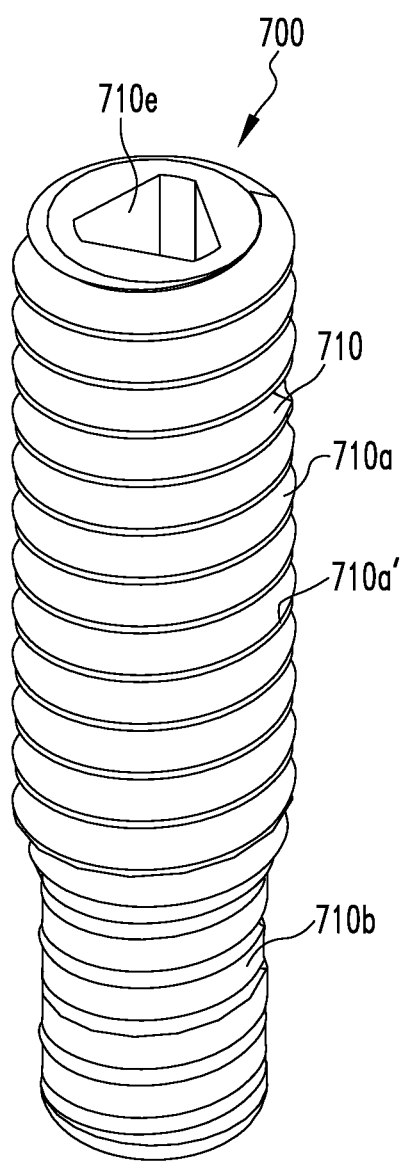
FIG. 32 shows a side elevational view of the insertion member of the anchor assembly of FIG. 28.
Figure 33:
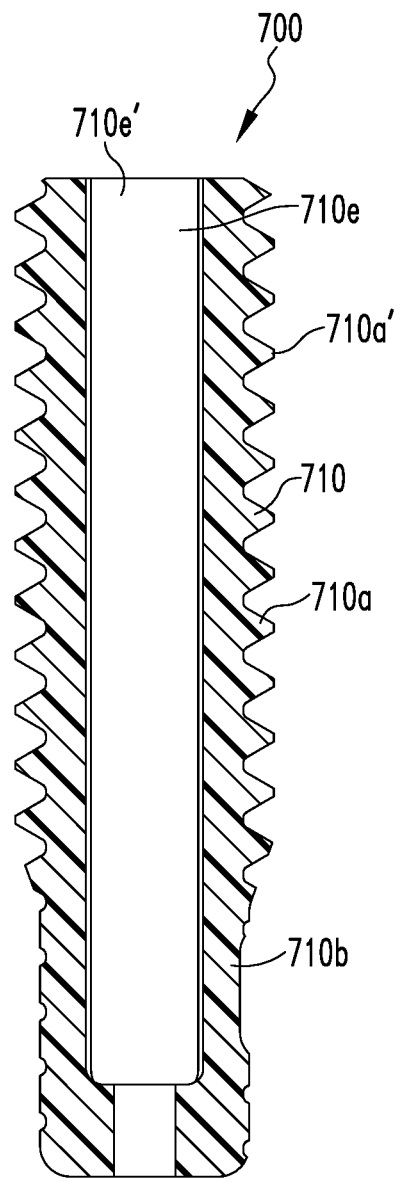
FIG. 33 shows a cross-sectional view of the insertion member of FIG. 32.
Figure 35:
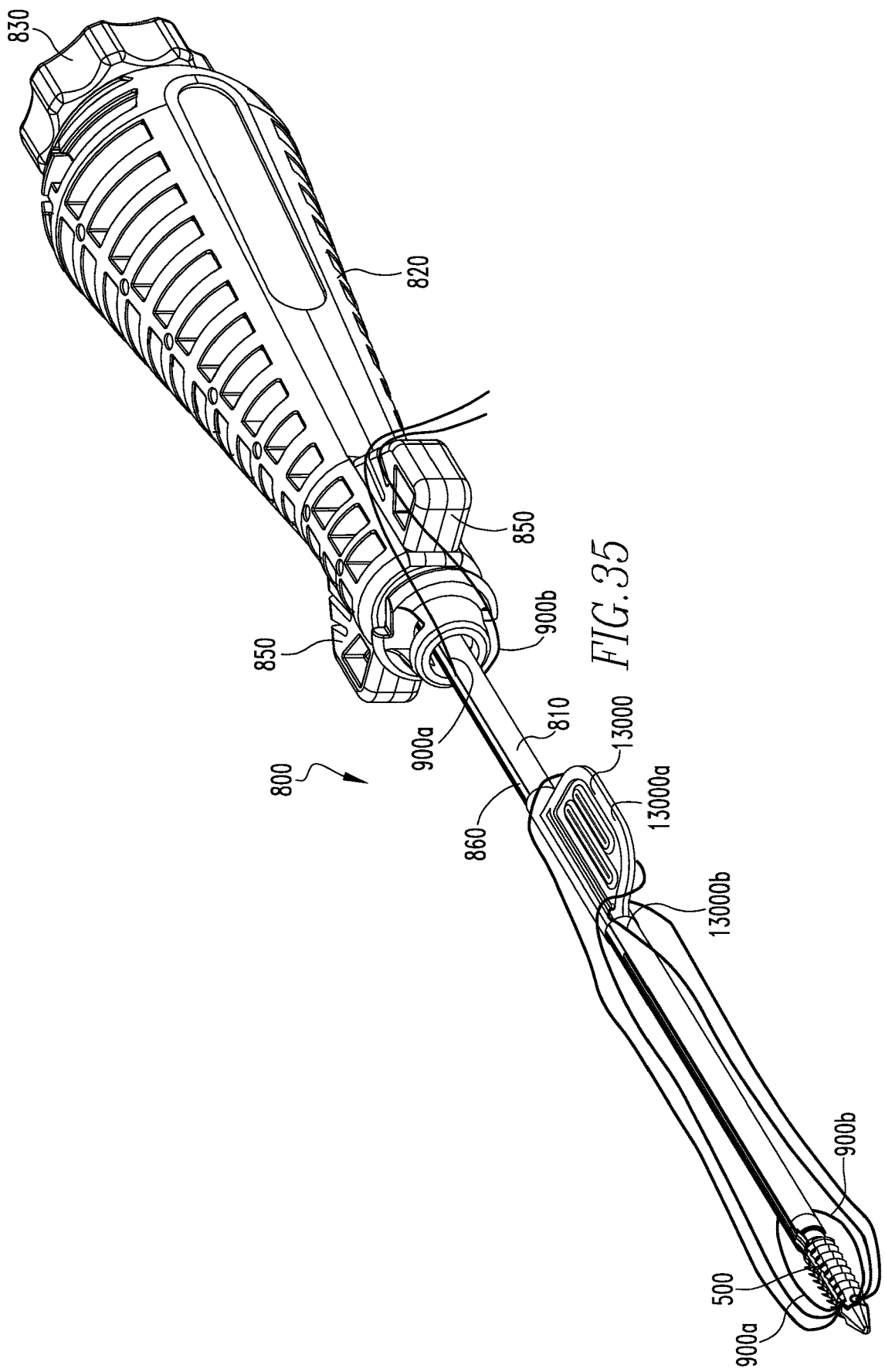
FIG. 35 shows an isometric view of the delivery device and anchor assembly of FIGS. 28 and 34.

FIGS. 45-50 show anchor assemblies 1300,1400,1500 similar to the anchor assemblies 10 of FIGS. 1, 8, and 28. The anchor assemblies 1300,1400,1500 are similar to the anchor assemblies 10,100,500 of FIGS. 1, 8, and 28 and the anchor assemblies shown and described in US Patent Application Publication No. 20090112270, the disclosure of which is incorporated herein by reference in its entirety, and the '869 publication mentioned above. FIGS. 45-50 only show the anchors 1310,1410,1510 of the assemblies 1300, 1400,1500. Although for the purposes of this disclosure, an insertion member, similar to the insertion members shown in the above mentioned figures and publications, would also be used with the anchors 1310,1410,1510. However, it is possible that the anchors 1310,1410,1510 could be used without insertion members, thereby being used in a similar manner to anchors 1000,1100,1200 during surgery.

Figure 45:
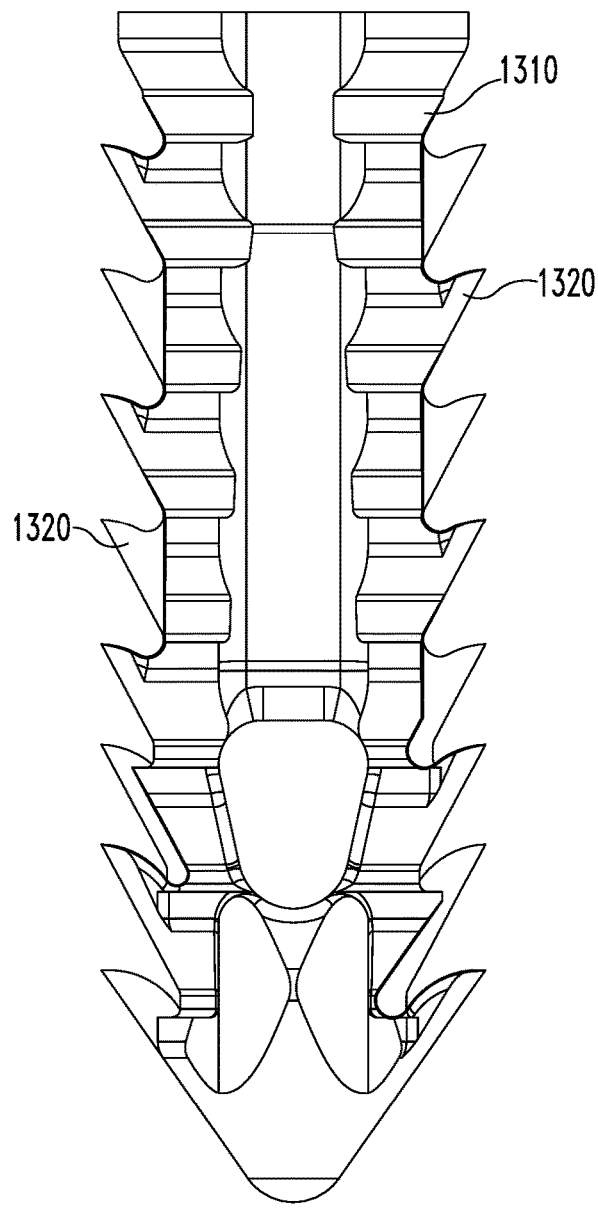
FIG. 45 shows a side view of a fourth embodiment of the anchor assembly of the present disclosure.
Figure 46:
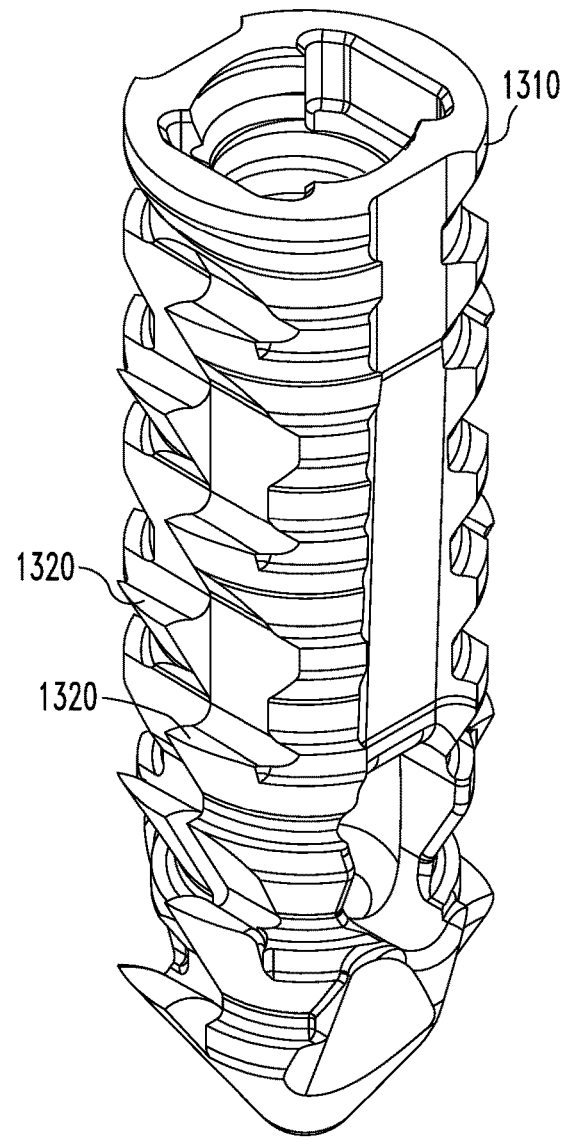
FIG. 46 shows a side elevational view of the anchor assembly of FIG. 45.
Figure 47:
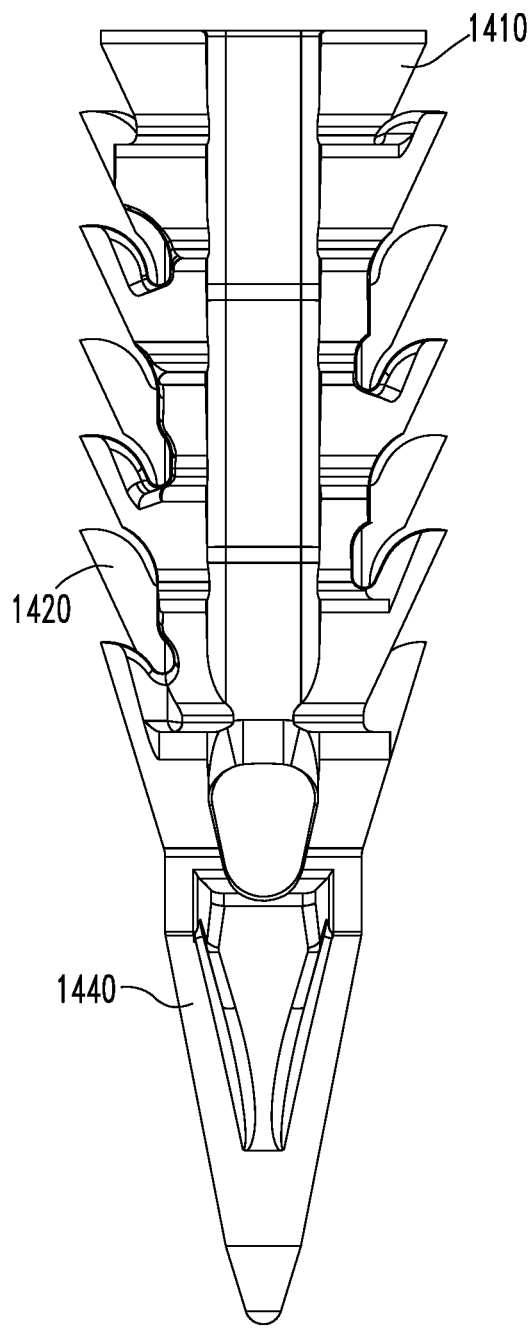
FIG. 47 shows a side view of a fifth embodiment of the anchor assembly of the present disclosure.
Figure 48:
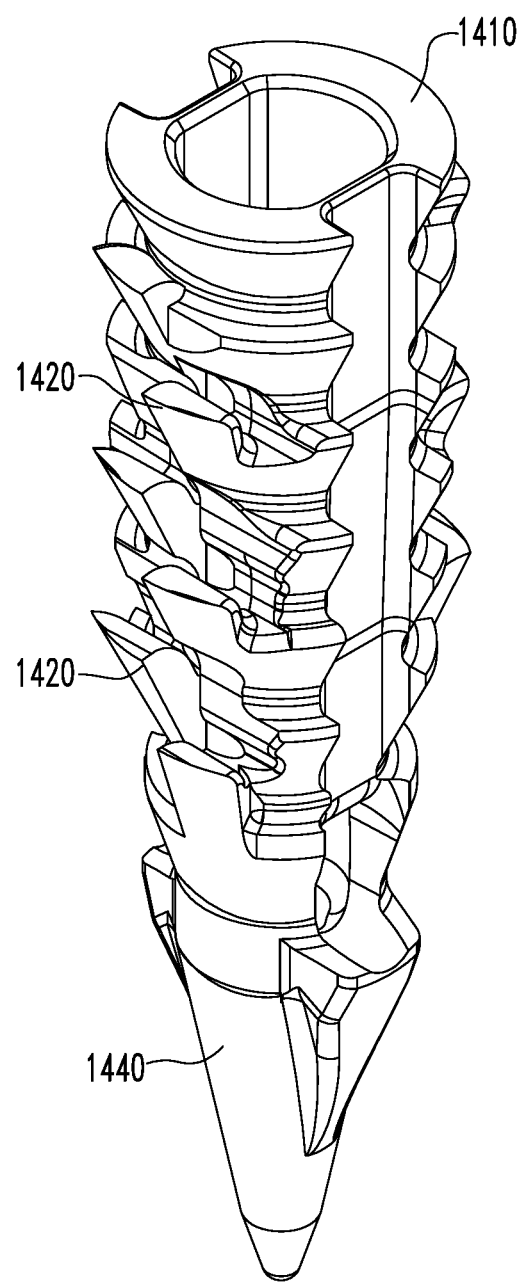
FIG. 48 shows a side elevational view of the anchor assembly of FIG. 47.
Figure 49:
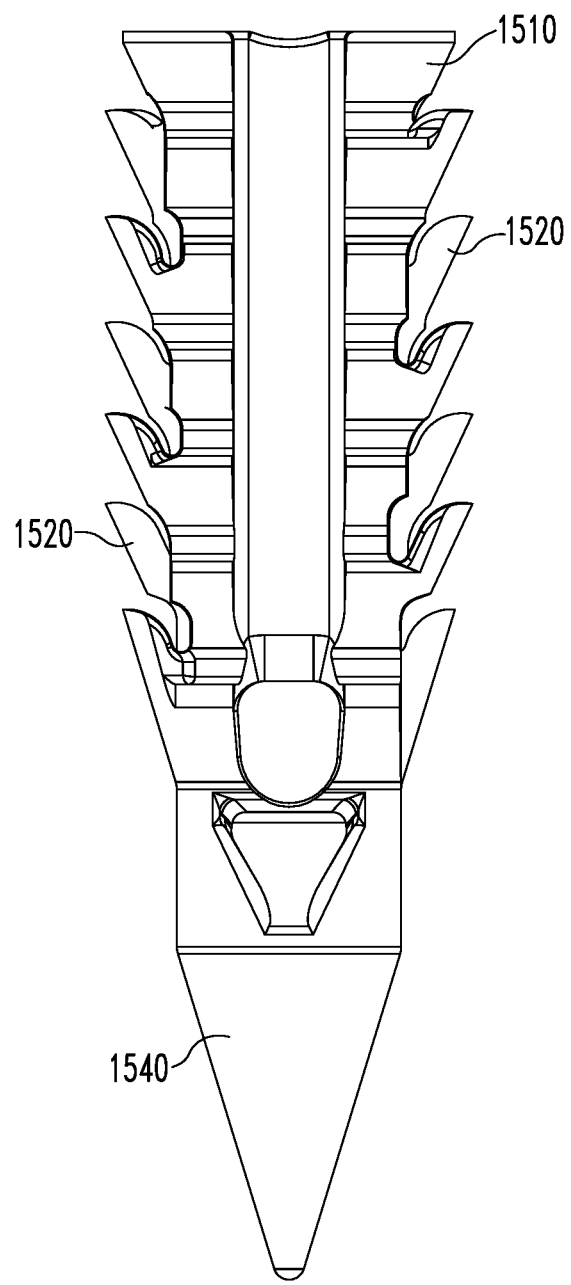
FIG. 49 shows a side view of a sixth embodiment of the anchor assembly of the present disclosure.
Figure 50:
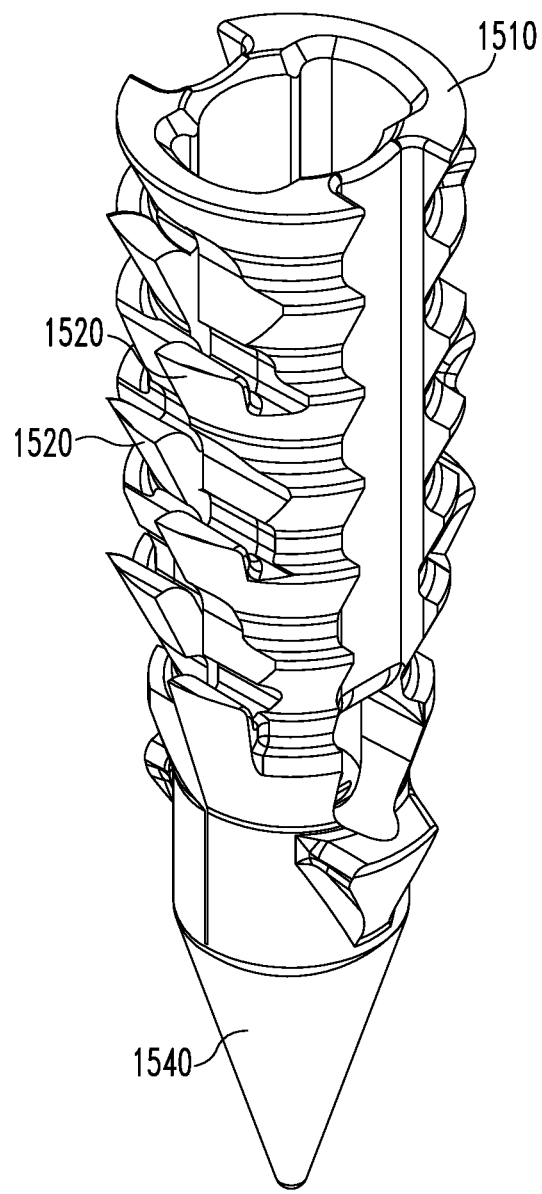
FIG. 50 shows a side elevational view of the anchor assembly of FIG. 49.

FIGS. 45-46 show an anchor 1310 having barbs 1320 that extend outward from the body 1330 of the anchor 1310 and along its entire length on both sides. The barbs 1320 alternate in direction along the length of the anchor 1310. Similar to wings 680, extending the barbs 1320 outward from the body 1330 increases the overall surface area of the barbs 1320 and allows flexibility, which improves resistance to anchor pull-out, thereby reducing the possibility of removal of the anchor 1300 when inserted into bone. FIGS. 47-50 show anchors 1410,1510, which include barbs 1420, 1520, similar in design and orientation, to barbs 1320 of anchor 1310. Unlike anchor 1310, the barbs 1420,1520 do not extend along the entire length of the anchor 1410,1510 and the distal end 1440,1540 of the anchor 1410,1510 is pointed thereby making it possible to insert the anchor 1410,1510 into bone without first creating a hole in the bone.

FIGS. 51 and 52 show an anchor 1610 that includes an outer body 1620 and an inner body 1630 disposed within the outer body 1620. The outer body 1620 includes an outer surface 1621 having wings 1622, similar to wings 680, and an inner cavity 1623. The distal end 1624 of the inner cavity 1623 includes a first feature 1625 and a second feature 1626, which will be more fully explained below in relation to the inner body 1630. Similar to the anchors described above, the outer body 1620 also includes a transverse hole 1627 and slots 1628. Similar to the anchors described above, the inner body 1630 includes a threaded inner cavity 1631, a through hole 1632, a proximal portion 1633, and a distal portion 1634. The inner body 1630 includes a first feature 1635 and a second feature 1636, both of which are located between the proximal and distal portions 1633,1634 and which will be more fully explained below in relation to the outer body 1620. The inner body 1630 is disposed within the outer body 1620 such that the outer body first feature 1625 is located within the inner body first feature 1635 and the outer body second feature 1626 is located within the inner body second feature 1636. The first features 1625,1635 are shaped so as to substantially reduce the possibility of the inner body 1630 rotating in relation to the outer body 1620 during repair, as will be more fully described below. The second features 1626,1636 are shaped so as to substantially reduce the possibility of the inner body 1630 from moving axially in relation to the outer body 1620 during insertion of the anchor 1610 into bone, as will be more fully described below. Additionally, the through holes 1627,1632 are aligned.

Similar to anchors 1310,1410,1510, anchor 1610 is part of an anchor assembly. However, for clarity purposes, the anchor 1610 is shown without an inner member. The distal portion 1634 of the inner body 1630 is pointed and the proximal portion 1633 does not extend the entire length of the inner cavity 1623, the purposes of which will be described later.

During insertion of the anchor 1610 into bone, a delivery device 1700, similar to delivery device 800, is used. For clarity purposes, only the outer member 1710a of the shaft 1710 is shown in FIGS. 51 and 52. The outer member 1710a is inserted into the anchor 1610 such that the square-shaped tip 1710c is inserted into the inner cavity 1623. The tip 1710c engages the inner body 1630 such that there is a clearance 1800 between the distal end 1710a' of the shaft 1710 and the anchor 1610. During insertion of the anchor 1610 into bone, the outer member 1710a only engages the inner body 1630, thereby asserting all of the axial force of the outer member 1710a on the inner body 1630, rather than the outer body 1620. The cooperation of the second features 1626,1636 substantially reduces the possibility of the inner body 1630 becoming unlocked from the outer body 1620 during axial insertion of the anchor 1610 into the bone. After insertion of the anchor 1610 into bone, a threaded inner member is rotationally inserted into the cavity 1631 via the use an inner member on the delivery device 1700, similar to the method of repair described above. During rotational insertion of the inner member into the cavity 1631, the cooperation of the first features 1625,1635 substantially reduces the possibility of rotation of the inner body 1630 in relation to the outer body 1620. The pointed distal portion 1634 of the inner body 1630 allows for insertion of the anchor 1610 into bone without having to create a hole in the bone prior to insertion.

For the purposes of this disclosure, the inner body 1630 is made from a metal material and the outer body 1620 is made from a polymer material. The outer and inner bodies 1620,1630 are coupled to each other via an interference fit or overmolding. However, other materials and manners of coupling may be used.

Figure 53:
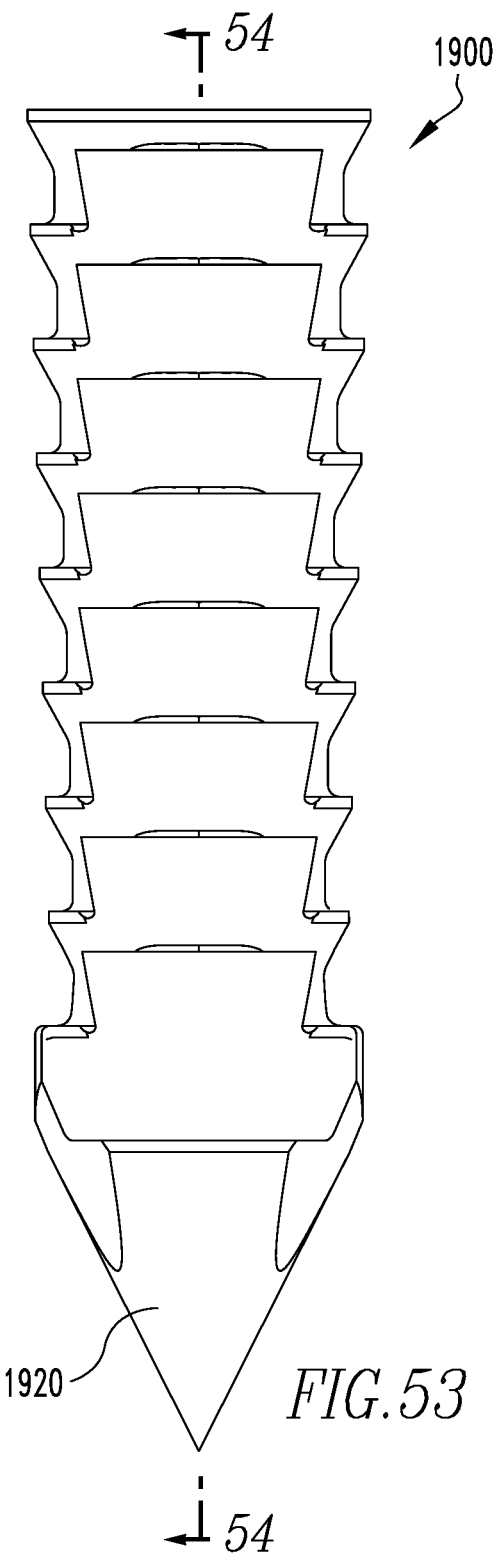
FIG. 53 shows a side view of an eighth embodiment of the anchor assembly of the present disclosure.
Figure 54:
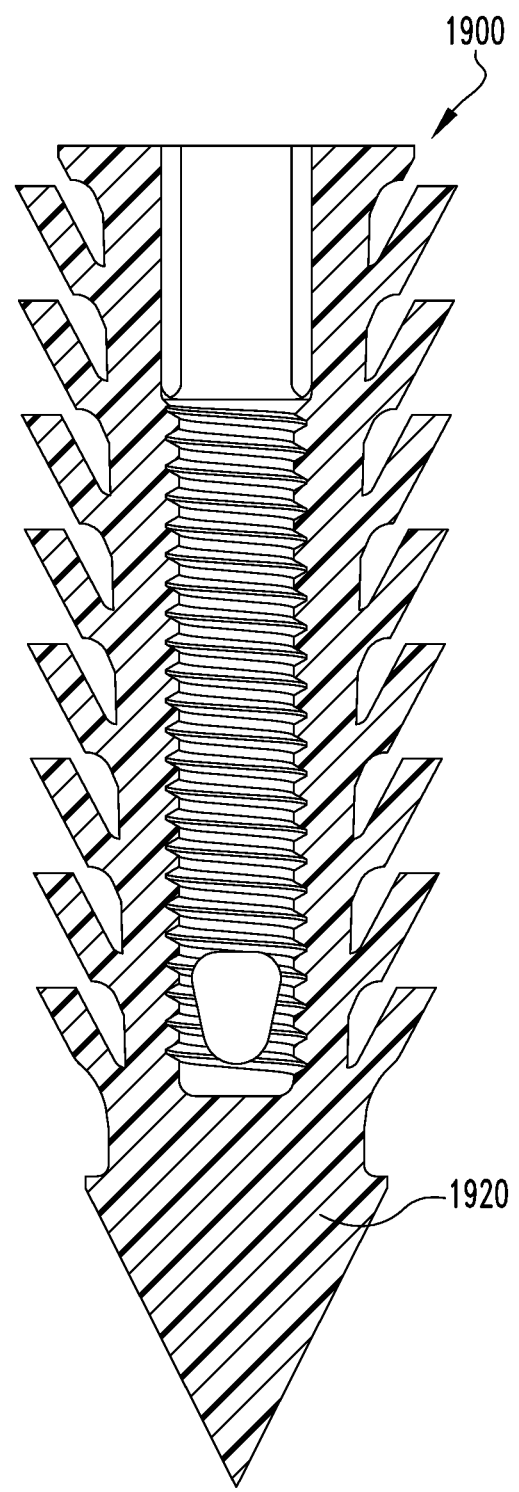
FIG. 54 shows a cross-sectional view of the anchor assembly of FIG. 53.

FIGS. 53 and 54 show an anchor 1900 similar to the anchor 600, albeit with a distal portion 1920 that is pointed enough to allow for insertion of the anchor 1900 into bone without first creating a hole in bone.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of repairing a tissue comprising:
preparing a bone hole adjacent to the tissue;
passing a length of suture through a through-hole of an anchor body, the anchor body defining a cavity extending from a proximal end of the anchor body, the cavity having a bottom surface spaced from a distal tip of the anchor body, the anchor body also having a plurality of wings extending from an outer surface of the anchor body, the through-hole intersecting the cavity defining first and second openings of the through-hole on opposing sides of the cavity;
inserting the anchor body and the length of suture into the bone hole with an insertion instrument operatively coupled to the anchor body;
adjusting a tension on the length of suture; and
after inserting and adjusting, axially advancing an insertion member along the anchor body cavity towards the length of suture to secure the length of suture with the insertion member and anchor body; wherein the insertion member has a distal portion that defines a length having a diameter along the entire distal portion length that is smaller than a diameter of a proximal portion of the insertion member, and wherein axially advancing the insertion member comprises axially advancing the insertion member from a first position wherein the entire insertion member is proximal the through-hole, up to a second position wherein the distal portion length covers the through-hole from a point proximal of a proximal edge of the through-hole to a point distal of a distal edge of the through-hole.

2. The method of claim 1 further comprising fixing at least one end of the length of suture to a suture holder of the insertion instrument after passing the length of suture through the through-hole; and then cutting the at least one end of the length of suture after axially advancing the insertion member, to release the length of suture from the insertion instrument.

3. The method of claim 1 wherein the cavity defines a threaded cavity and the insertion member is threadingly coupled to the threaded cavity and wherein axially advancing the insertion member includes rotating the insertion member to move the insertion member to the second position.

4. The method of claim 1 wherein in the first position, the insertion member is partially inserted within the anchor body cavity, and wherein the insertion member is in the first position while inserting the anchor body into the bone hole.

5. The method of claim 1 further comprising:
axially retracting the insertion member and adjusting the tension on the length of suture after axially advancing the insertion member; followed by
axially advancing the insertion member again to secure the length of suture with the anchor body.

6. The method of claim 1 further comprising coupling the length of suture to a location spaced away from the bone hole before passing the length of suture through the through-hole of the anchor body.

7. The method of claim 6 wherein coupling the length of suture to a location spaced away from the bone hole comprises inserting a tissue anchor operatively coupled to the length of suture into a tissue spaced away from the bone hole.

8. The method of claim 7 wherein adjusting the tension on the length of suture adjusts the tension between the tissue anchor spaced away from the bone hole and the anchor body.

9. A method of repairing a tissue comprising:
preparing a bone hole adjacent to the tissue;
drawing a length of suture through a through-hole of an anchor body the anchor body defining a threaded cavity extending from a proximal end of the anchor body, the through-hole intersecting the cavity defining first and second openings on opposing sides of the cavity;
inserting the anchor body into the bone hole;
adjusting a tension on the length of suture; and
after drawing the length of suture through the through hole and inserting the anchor body, axially advancing an insertion member along the anchor cavity to secure the length of suture with the anchor body;
wherein the insertion member includes a threaded proximal portion configured to threadingly engage the threaded cavity, the insertion member also including a distal portion extending distally from the threaded proximal portion that has a diameter smaller than a diameter of the threaded proximal portion, and wherein axially advancing the insertion member covers the first and second openings entirely with the distal portion.

10. The method of claim 9 wherein while inserting the anchor body, the insertion member is threadingly coupled to the anchor body cavity and proximally spaced from the through-hole.

11. The method of claim 9 further comprising: coupling at least one end of the length of suture with an insertion instrument to couple the anchor body to the insertion instrument; and disconnecting the at least one end of the length of suture after axially advancing the insertion member, to release the insertion instrument from the anchor body.

12. The method of claim 9 further comprising: axially retracting the insertion member and adjusting the tension on the length of suture; followed by axially re-advancing the insertion member to secure the length of suture with the anchor body.

13. The method of claim 9 further comprising coupling the length of suture to a previously placed tissue anchor within a tissue adjacent the bone hole before drawing the length of suture through the through-hole.

14. The method of claim 13 wherein adjusting the tension on the length of suture adjusts the tension between the previously placed tissue anchor and the anchor body.

15. The method of claim 13 wherein adjusting the tension on the length of suture adjusts compression of a rotator cuff tissue disposed between the previously placed tissue anchor and the anchor body.

16. A method of repairing a tissue comprising:
preparing a bone hole adjacent to the tissue;
drawing a length of suture through a through-hole of an anchor body, the through-hole intersecting a longitudinal cavity extending through the anchor body, the longitudinal cavity having a bottom surface spaced away from a distal tip of the anchor body and the through-hole defining first and second openings on opposing sides of the longitudinal cavity;
with the length of suture drawn through the through-hole; inserting the anchor body into the bone hole;
adjusting a tension on the length of suture; and
once the tension is adjusted, axially advancing an insertion member into the longitudinal cavity to secure the length of suture with the anchor body;
wherein the insertion member has a distal portion that defines a smaller diameter than a diameter of a proximal portion of the insertion member, wherein axially advancing the insertion member covers the entire through-hole with the smaller diameter distal portion from a point proximal of a proximal edge of the through-hole to a point distal of a distal edge of the through-hole.

17. The method of claim 16 further comprising: axially retracting the insertion member and adjusting the tension on the length of suture; followed by axially re-advancing the insertion member to secure the length of suture with the anchor body.

18. The method of claim 17 wherein adjusting the tension on the length of suture adjusts the tension between a previously placed tissue anchor and the anchor body.

19. The method of claim 16 further comprising coupling the length of suture to a previously placed tissue anchor couple to a tissue adjacent the bone hole before drawing the length of suture through the through-hole.

20. The method of claim 16 further comprising coupling at least one end of the length of suture with a handle of an insertion instrument before inserting the anchor body into the bone hole.

* * * * *